United States Patent
Kirkland et al.

(10) Patent No.: US 6,884,417 B2
(45) Date of Patent: *Apr. 26, 2005

(54) MONOCLONAL ANTIBODIES IMMUNOREACTIVE WITH LIPOPOLYSACCHARIDE BINDING PROTEIN (LBP) AND METHODS OF THEIR USE

(75) Inventors: Theo Kirkland, La Jolla, CA (US); Peter Tobias, San Diego, CA (US); Richard Ulevitch, Del Mar, CA (US); Ann Moriarty, Poway, CA (US); Didier Leturcq, San Diego, CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/858,279

(22) Filed: May 15, 2001

(65) Prior Publication Data

US 2001/0029292 A1 Oct. 11, 2001

Related U.S. Application Data

(62) Division of application No. 09/081,350, filed on May 19, 1998, now Pat. No. 6,232,080, which is a division of application No. 08/679,944, filed on Jul. 15, 1996, now Pat. No. 5,753,504, which is a continuation of application No. 08/153,364, filed on Nov. 16, 1993, now abandoned.

(51) Int. Cl.⁷ ...................... A61K 39/395; A61K 39/40; A61K 39/42; A61K 39/00; A61K 39/38
(52) U.S. Cl. ................... 424/137.1; 424/130.1; 424/135.1; 424/136.1; 424/137.1; 424/142.1; 424/143.1; 424/145.1; 424/149.1; 424/156.1; 424/164.1; 424/178.1; 424/184.1; 435/329; 435/332; 435/334; 435/344.1; 436/512; 436/547; 436/548

(58) Field of Search ............. 424/130.1, 135.1, 424/136.1, 137.1, 142.1, 143.1, 149.1, 156.1, 164.1, 178.1, 184.1, 124.1, 145.1, 278.1; 435/329, 332, 334, 344.1, 70.21; 436/512, 547, 548; 530/387.1

(56) References Cited

U.S. PATENT DOCUMENTS 5,753,504 A * 5/1998 Kirkland et al. ............ 435/340

OTHER PUBLICATIONS

Leturcq et al. 1992. J. Cell. Biochem. 16C:161.*

Martin et al. 1992. J. Clin. Investigations. 90:2209–2219.*

Pugin et al. 1993, PNAS. 90:2744–2448.*

Gallay, et al., "Competition Between LPS–Binding Protein (LBP) and Anti–LPS Antibody in LPS–Induced TNF Secretion of Human Monocytes (MO)", *Experientia 48*: p. A66, Abstract 384 (1992).

(Continued)

*Primary Examiner*—L. F. Smith
*Assistant Examiner*—J. Hines
(74) *Attorney, Agent, or Firm*—Thomas Fitting; Michael J. McCarthy

(57) ABSTRACT

The present invention concerns a method of treating LBP-mediated LPS-induced myeloid cell activation comprising administering a therapeutically effective amount of an anti-LBP monoclonal antibody molecule. A therapeutic composition comprising anti-LBP antibody molecules in a pharmaceutically acceptable excipient is also contemplated.

7 Claims, 4 Drawing Sheets

OTHER PUBLICATIONS

Harlow, et al., "Antibodies: A Laboratory Manual" (1998).

Landmann, et al., "Effect of Cytokines and Lipopolysaccharide on CD14 Antigen Expression in Human Monocytes and Macrophages", *J. of Cell. Biochem. 47*: 317–329.

Leturcq, et al., "Generation of Monoclonal Antibodies to Human LBP and Their Use in the Detection of LBP Protein in Serum", *Journal of Cellular Biochemistry*, Supplement 16, Part C, p. 161, Abstract CB109 (1992).

Martin, et al., "Lipopolysaccharide Binding Protein Enhances the Responsivesness of Alveolar Macrophages to Bacterial Lipopolysaccharide", *Journal of Clinical Investigations 90*: 2209–2219 (1992).

Pugin, et al., "Lipopolysaccharide Activation of Human Endothelial and Epithelial Cells is Mediated by Lipopolysaccharide–Binding Protein and Soluble CD14", *Proc. Natl. Acad. Sci. USA 90*: 2744–2748 (1993).

Schutt, et al., "Human Monocyte Activation Induced by an Anti–Monoclonal Antibody", *Immuno. Letters 19*: 321–328 (1988).

Tobias, et al., "Participation of Lipopolysaccharide–binding Protein in Lipopolysaccharide–dependent Macrophage Activation", *Am. J. Respir. Cell Mol. Biol. 7*: 239–245 (1992).

Waldmann, "Monoclonal Antibodies in Diagnosis and Therapy", *Science 252*: 1657–1662 (1991).

Weir, "Vol. 3 Application of Immunological Methods", *Blackwell Scientific Publicaitons* (1978).

Tobias, et al., "Isolation of a Lipopolysaccharide–Binding Acute Phase Reactant From Rabbit Serum", *J. Exp. Med.*, 164: 777–793 (1986).

Tobias, et al., "Identification of a Lipid A Binding Site in the Acute Phase Reactant Lipopolysaccharide Binding Protein", *J. Biol. Chem.*, 264: 10867–10871 (1989).

Wright, et al., "CD14, a Receptor for Complexes of Lipopolysaccharide (LPS) and LPS Binding Protein", *Science*, 249: 1431–1433 (1990).

Schumann, et al., "Structure and Function of Lipopolysaccharide Binding Protein", *Science*, 249: 1429–1431 (1990).

* cited by examiner

MONOCLONAL ANTIBODIES IMMUNOREACTIVE WITH LIPOPOLYSACCHARIDE BINDING PROTEIN (LBP) AND METHODS OF THEIR USE

This is a division of application Ser. No. 09/081,350 filed May 19, 1998, now U.S. Pat. No. 6,232,080 which is a division of application Ser. No. 08/679,944, filed Jul. 15, 1996, now U.S. Pat. No. 5,753,504 which is a continuation of Ser. No. 08/153,364 filed on Nov. 16, 1993, now abandoned.

This invention was made with government support under Contract Nos. GM 37696 and AI 15136 by the National Institutes of Health. The government has certain rights in the invention.

DESCRIPTION

1. Technical Field

The present invention relates to monoclonal antibodies immunoreactive with lipopolysaccharide binding protein (LBP) and methods for using the antibodies. In addition, the invention relates to methods for detecting the presence of LBP in samples, and to therapeutic methods of using the antibodies for inhibiting LBP-mediated activation of cell of monocyte and macrophage lineage.

2. Background

Sepsis is a morbid condition induced by a toxin, the introduction or accumulation of which is most commonly caused by infection or trauma. The initial symptoms of sepsis typically include chills, profuse sweat, irregularly remittent fever, prostration and the like, followed by persistent fever, hypotension leading to shock, neutropenia, leukopenia, disseminated intravascular coagulation, adult respiratory distress syndrome and multiple organ failure.

Sepsis-inducing toxins have been found associated with pathogenic bacteria, viruses, plants and venoms. Among the well described bacterial toxins are the endotoxins or lipopolysaccharides (LPS) of the gram-negative bacteria. These molecules are glycolipids that are ubiquitous in the outer membrane of all gram-negative bacteria. While chemical structure of most of the LPS molecule is complex and diverse, a common feature is the lipid A region of LPS [Rietschel, E. Th. et al., in *Handbook of Endotoxins*, 1:187–214 eds. R. A. Proctor and E. Th. Rietschel, Elsevier, Amsterdam (1984)]; recognition of lipid A in biologic systems initiates many, if not all, of the pathophysiologic changes of sepsis. Because lipid A structure is highly conserved among all types of gram-negative organisms, common pathophysiologic changes characterize gram-negative sepsis.

Current concepts support the contention that the primary response of the host to LPS (including man) involves the recognition of LPS by cells of the monocyte/macrophage lineage, followed by the rapid elaboration of a variety of cell products including the general group known as cytokines. Other cell types believed to participate in sepsis and in particular in the response to LPS are polymorphonuclear leukocytes and endothelial cells; each of these cell types are also capable of responding to LPS with the elaboration of potent inflammatory substances.

LPS is believed to be a primary cause of death in humans during gram-negative sepsis, particularly when the symptoms include adult respiratory distress syndrome (ARDS). van Deventer et al., *Lancet*, 1:605 (1988); Ziegler et al., *J. Infect. Dis.*, 136:19–28 (1987). For instance, one particular cytokine, tumor necrosis factor alpha/cachectin (TNF), has recently been reported to be a primary mediator of septic shock. Beutler et al., *N. Eng. J. Med.*, 316:379 (1987). Intravenous injection of LPS endotoxin from bacteria into experimental animals and man produces a rapid, transient release of TNF. Beutler et. al., *J. Immunol.*, 135:3972(1985). Mathison et al., *J. Clin. Invest.* 81: 1925 (1988). Evidence that TNF is a critical mediator of septic shock comes primarily from experiments in which pretreatment of animals with anti-TNF antibodies reduces lethality. Beutler et al., *Science*, 229:869, (1985). Mathison et al., *J. Clin. Invest.* 81: 1925 (1988). These reports suggest that interruption of the secretion of TNF caused by LPS or other factors would ameliorate the often lethal symptoms of sepsis.

Upon introduction of LPS into the blood, LPS binds to a protein termed lipopolysaccharide binding protein (LBP). LBP is a 60 kD glycoprotein present at concentrations of less than 100 ng/ml in the serum of healthy animals and man. During the acute phase, LBP is synthesized by hepatocytes, and reaches concentrations of 30–50 ug/ml in serum. LBP can be purified from acute phase human and rabbit serum. Tobias, et al., *J. Exp. Med.*, 164:777–793 (1986). LBP recognizes the lipid A region of LPS and forms high affinity, 1:1 stoichiometric complexes with both rough and smooth form LPS. Tobias, et al., *J. Biol. Chem.*, 264:10867–10871 (1989). LBP bears N-terminal sequence homology with the LPS-binding protein known as bactericidal permeability-increasing factor, (BPI). Tobias, et al., *J. Biol. Chem.*, 263:13479–13481, (1988) BPI is stored in the specific granules of PMN [Weiss, et al., *Blood*, 69:652–659, (1987)] and kills gram negative bacteria by binding LPS and disrupting the permeability barrier. Weiss, et al., *J. Immunol.*, 132:3109–3115, (1984). In contrast to BPI, LBP is not directly cytotoxic for gram-negative bacteria [Tobias, et al., *J. Biol. Chem.*, 263:13479–13481, (1988)].

The macrophage/polymorphonuclear leukocyte differentiation antigen, CD14, binds LPS in the presence of LBP when present as LPS-LBP complexes, and this binding event activates cellular responses. Wright et al., *Science*, 249:1431–1433 (1990); Lee et al., *J. Exp. Med.*, 175:1697–1705 (1992). Although it is believed that LPS-LBP binding to CD14 is the important event in LPS-induced activation of myeloid cell lines, it remains unclear what parameters influence LBP-dependent binding of LPS by CD14, and particularly what stoichiometric parameters are involved in the LBP-dependent CD14:LPS interaction.

Monoclonal antibodies immunoreactive with LBP have not been described that interfere with LPS:CD14-mediated cell activation. Therefore, there continues to be a need for reagents that interact with LBP for elucidation and intervention of LBP function.

BRIEF DESCRIPTION OF THE INVENTION

The present invention was born out of the discovery that monoclonal antibodies immunoreactive with LBP can interfere with LPS:CD14 function, and particularly that inhibit LPS binding to CD14. Surprisingly, anti-LBP antibodies are described that do not inhibit LPS binding to LBP, and yet interfere with LPS:CD14 binding.

Thus, in one embodiment the invention contemplates an monoclonal antibody that immunoreacts with lipopolysaccharide (LPS) binding protein (LBP) but does not substantially inhibit LBP binding to LPS. Preferably, the LBP is human LBP.

Preferably, the monoclonal antibody also inhibits LBP-mediated binding of LPS to CD14. More preferably, the monoclonal antibody inhibits LBP-mediated LPS-dependent activation of myeloid cells, and still more preferably the monoclonal antibody inhibits LBP-mediated LPS-dependent secretion of tumor necrosis factor from myeloid cells.

Also contemplated are hybridoma cell lines that produce a monoclonal antibody of this invention.

In a further embodiment, the invention contemplates therapeutic compositions, typically in unit dose form, useful for inhibiting LPS binding to CD14, and therefore can be used for preventing or ameliorating the symptoms of LPS mediated cell activation, including cytokine production and sepsis. The compositions comprise a pharmaceutically acceptable carrier containing one or more of an anti-LBP antibody that acts as an LBP antagonist, as an active ingredient.

In preferred embodiments, a therapeutic composition of this invention further contains, as active ingredients an agent known to prevent or ameliorate the symptoms of sepsis, such as an antibiotic, steroid, anti-TNF antibody, a TNF antagonist, soluble CD14 and the like, either alone, in sub-combination or combination.

The present invention also contemplates administering, preferably intravenously, to a patient at risk for or suffering the symptoms of LBP-mediated LPS-dependent cell activation a therapeutically effective amount of an anti-LBP antibody. The method can be practiced alone or in combination with the substantially simultaneous administration of other therapeutic modalities known to prevent or ameliorate the symptoms of LBP-mediated LPS-dependent cell activation, including treatment with one or more of an antibiotic, steroids, anti-TNF antibody, TNF antagonist and the like.

Diagnostic methods for detecting LBP in a sample using one or more anti-LBP-antibodies are also contemplated as are kits useful for the detection of LBP containing anti-LBP antibodies.

A major advantage of the present invention lies in the discovery that the monoclonal antibodies described herein not only immunoreact with LBP but do not substantially interfere with LPS binding to LBP. This is significant because LPS is therefore taken up by its natural partner, LBP, and is not free to participate in other LPS-mediated LBP-independent events such as where LPS could initiate other undesirable events besides LBP-mediated LPS-dependent cell activation. Furthermore, certain of the anti-LBP antibodies described herein are effective at inhibiting LPS binding to CD14 independent of the sequence of binding events between LPS and LBP and between LBP and anti-LBP antibodies. In other words, anti-LBP antibodies can inhibit LPS binding to CD14 whether added to LBP-containing samples before or after LPS has been allowed to bind to LBP, such as either before of after LBP-mediated LPS-dependent cell activation has begun.

BRIEF DESCRIPTION OF THE DRAWINGS

In the Figures forming a portion of the disclosure of this invention.

DETAILED DESCRIPTION OF THE INVENTION

A. Definitions

Figure 1:
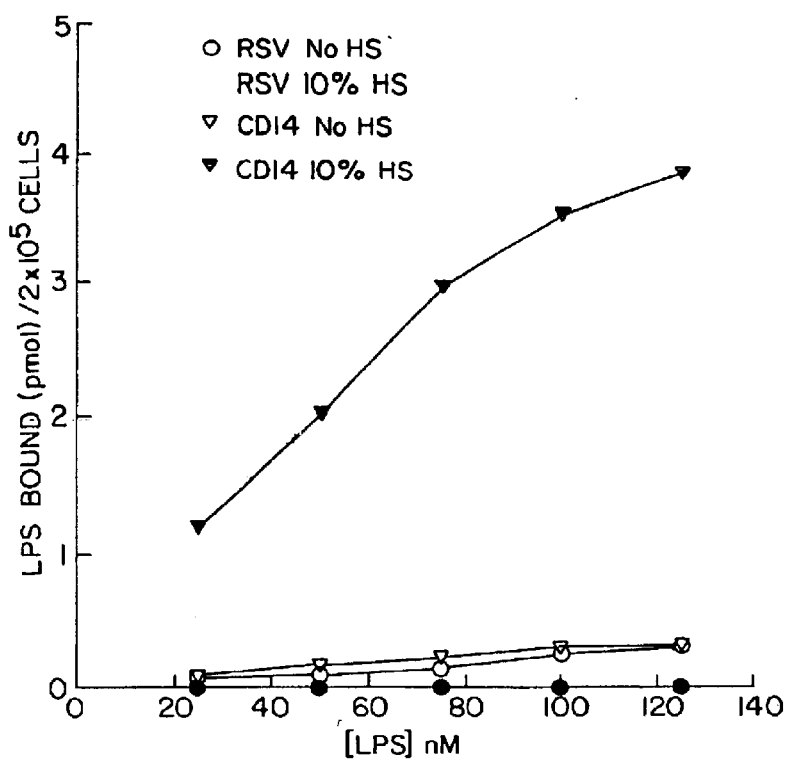
FIG. 1 illustrates LPS binding in picomoles (pMol) at different LPS concentrations ranging from 20 to 120 nM. RSV-CHO cells are cells transfected with the RSV vector; CD14-CHO cells are cells that express CD14. HS-human serum. Open and closed circles respectively represent assay results with RSV-CHO cells without serum and RSV-CHO with 10% serum. Open and closed triangles respectively represent CD14-CHO cells without serum and CD14-CHO cells with serum. The binding was done at 10C as described in Example 2A. The data points represent the means determinations; the standard deviations are smaller than the symbols.

Antibody: The term antibody in its various grammatical forms is used herein to refer to immunoglobulin molecules and immunologically active portions of immunoglobulin molecules, i.e., molecules that contain an antibody combining site or paratope. Exemplary antibody molecules are intact immunoglobulin molecules, substantially intact immunoglobulin molecules and portions of an immunoglobulin molecule, including those portions known in the art as Fab, Fab', F(ab')$_2$ and F(v).

Antibody Combining Site: An antibody combining site is that structural portion of an antibody molecule comprised of a heavy and light chain variable and hypervariable regions that specifically binds (immunoreacts with) an antigen. The term immunoreact in its various forms means specific binding between an antigenic determinant-containing molecule and a molecule containing an antibody combining site such as a whole antibody molecule or a portion thereof.

Monoclonal Antibody: A monoclonal antibody in its various grammatical forms refers to a population of antibody molecules that contain only one species of antibody combining site capable of immunoreacting with a particular epitope. A monoclonal antibody thus typically displays a single binding affinity for any epitope with which it immunoreacts. A monoclonal antibody may therefore contain an antibody molecule having a plurality of antibody combining sites, each immunospecific for a different epitope, e.g., a bispecific monoclonal antibody. Although historically a monoclonal antibody was produced by immortalization of a clonally pure immunoglobulin secreting cell line, a monoclonally pure population of antibody molecules can also be prepared by the methods of the present invention.

Pharmaceutically acceptable refers to molecular entities and compositions that are physiologically tolerable and do not typically produce an allergic or similar untoward reaction, such as gastric upset, dizziness and the like, when administered to a human.

B. Monoclonal Antibodies

The present invention relates to monoclonal antibodies immunoreactive with lipopolysaccharide (LPS) binding protein (LBP).

LBP is present in the serum of mammals and is known to participate in LPS-dependent cell activation, as described herein. Thus, a monoclonal antibody of this invention immunoreacts with any of a variety of LBP proteins, depending upon the species of origin of the LBP protein. As is well known, LBP is highly conserved across species. However, there are sufficient differences in the amino acid residue sequences that monoclonal antibodies of the present invention are species specific, and others immunoreact with LBP isolated from different species. Exemplary anti-LBP antibodies are described herein that are species specific, and others are described that cross species. A preferred anti-LBP monoclonal antibody immunoreacts with human LBP.

A unique feature of the anti-LBP antibodies of the present invention is the capacity to immunoreact with LBP and not inhibit the ability of LBP to bind LPS. Thus, an anti-LBP antibody of this invention immunoreacts with LBP but does not substantially inhibit LBP binding to LPS. By "substantially" in this context is meant that LPS binds to LBP in the presence of the antibody [at 10 micrograms (ug) antibody per milliliter (ml)] to the extent of at least about 50% of LPS binding to LBP in the absence of antibody, preferably at least about 80%, more preferably at least about 95%, and particularly indistinguishably when compared to normal binding in the absence of antibody. Assays for the detection of LPS binding to LBP are well known in the art, and particularly are described in the Examples.

The above feature provides the advantage that the antibody can bind LBP whether or not LPS is already present and complexed with LBP. This feature provides advantages in diagnostic methods for assaying for the presence of LBP in a sample, such as a body fluid, e.g., blood, serum or plasma, because the LBP levels are determined irrespective of LPS.

Furthermore, in therapeutic applications, the above feature provides unique advantages because LPS is known to effect a variety of deleterious physiological events, and binding of LPS by LBP is viewed as beneficial insofar as LBP binding serves to remove soluble LPS from the circulation where it may exert LBP-independent effects. In other words, LBP binding of LPS serves to scavenge free LPS away from the circulation, reducing LBP-independent LPS-mediated events.

A preferred anti-LBP monoclonal antibody has the binding specificity of an anti-human LBP monoclonal antibody of this invention. A preferred anti-human LBP monoclonal antibody (Mab) has a binding specificity for an epitope defined by Mab 1E8, Mab 2B5, Mab 4D7, Mab 5C5, Mab 6B6, Mab 8C9, Mab 8F5, Mab 18G4, or Mab 24B7. Preferred is the particular monoclonal antibody designated herein as Mab 1E8, Mab 2B5, Mab 4D7, Mab 5C5, Mab 6B6, Mab 8C9, Mab 8F5, Mab 18G4, or Mab 24B7, described further herein and in the Examples.

The above antibodies have a variety of utilities, including, but not limited to the use as diagnostic reagents for the detection of LBP in samples as described further herein. In particular, two cross-reactive groups are described herein, each group defined by their ability to compete for binding to LBP in the solid phase. A first group is defined by Mab 1E8, and a second group is defined by 2B5, and other members of the "2B5" group based on competition studies to include Mab 4D7, Mab 5C5, Mab 6B6, Mab 8C9, Mab 8F5, Mab 18G4, and Mab 24B7. Competition studies are well known in the art and can be conducted in a variety of ways to identify additional antibodies in the respective 1E8 and 2B5 groups. Exemplary competition study methods are described herein.

In particular, a "sandwich" immunoassay format is provided by the availability of two groups of antibodies that do not compete, where members of one group are used as the "capture" antibody, and members of the other group are used as the "detecting" antibody.

In another embodiment, the invention describes an anti-LBP monoclonal antibody that immunoreacts with LBP but does not substantially inhibit LBP binding to LPS, and that further inhibits LBP-mediated binding of LPS to CD14. Methods for determining the ability of LPS to bind to CD14 by a LBP-mediated mechanism are described in the Examples, although other methods are apparent to one skilled in the art. An exemplary antibody according to this embodiment is a monoclonal antibody having the binding specificity for the epitope defined by Mab 1E8, Mab 2B5, Mab 4D7, Mab 5C5, Mab 6B6, Mab 18G4, or Mab 24B7. Particularly preferred are the specific antibodies recited hereinabove.

In still another preferred embodiment, the invention contemplates an anti-LBP monoclonal antibody that immunoreacts with LBP but does not substantially inhibit LBP binding to LPS, and that further inhibits LBP-mediated LPS-dependent activation of myeloid cells, and therefore inhibits the processes which attend cell activation. These events are well known in the art, and include, but are not limited to LBP-mediated LPS-dependent secretion of cytokines, such as tumor necrosis factor, from myeloid cells, and in more severe cases, endotoxemia and sepsis. Methods for using such inhibitory antibodies are described herein.

A preferred anti-LBP monoclonal antibody in this embodiment that inhibits LBP-mediated LPS-dependent cell activation is a monoclonal antibody having a binding specificity for the epitope defined by MAB 2B5. Particularly preferred is the monoclonal antibody Mab 2B5 produced by a hybridoma cell line having ATCC accession number HB 11491.

Laboratory methods for preparing monoclonal antibodies are well known in the art. See, for example, Harlow et al., *Antibodies: A Laboratory Manual*, Cold Spring Harbor Laboratory, New York, 1988. The monoclonal antibodies of the present invention were prepared by immunizing purified LBP protein isolated from any of a variety of mammalian species into a mammal, e.g., a mouse, rabbit, goat, human and the like mammal. The antibody-producing cells in the immunized mammal are isolated and fused with myeloma or heteromyeloma cells to produce hybrid cells (hybridoma). The hybridoma cells producing the monoclonal antibodies are utilized as a source of the desired monoclonal antibody.

LBP can be purified from a variety of mammalian species, although human LBP is particularly preferred. A preferred method for the preparation of human LBP was described by Schumann et al., *Science*, 249:1429–1431 (1990), the teachings of which are incorporated by reference. Equivalent purification methods can readily be applied to the isolation of LBP from other mammalian species.

A monoclonal antibody with a claimed specificity, and like monoclonal antibodies with like specificity, are useful in the diagnosis and immunotherapy of LBP-mediated, LPS-induced disease.

The term "LBP-mediated, LPS-induced disease" means any disease caused, directly or indirectly, by LPS in which LBP is required to present LPS to myeloid cells. Such diseases are generally well known, and include conditions attendant with cytokine release, myeloid cell activation, endotoxemia and in advanced cases of LPS or endotoxin exposure, sepsis.

Thus, in one aspect, the present invention is directed to monoclonal antibodies which are reactive with a site on LBP that does not interfere with LPS binding, and cell lines which produce such antibodies. The isolation of cell lines producing monoclonal antibodies of the invention is described in great detail further herein, and using routine screening techniques which permit determination of the elementary immunoreaction and neutralization patterns of the monoclonal antibody of interest. Thus, if a monoclonal antibody being tested binds LBP and exhibits the desired properties described herein, then the monoclonal antibody being tested and the monoclonal antibody produced by the cell lines of the invention are considered equivalent.

It is also possible to determine, without undue experimentation, if a monoclonal antibody has the same (i.e., equivalent) specificity as a monoclonal antibody of this invention by ascertaining whether the antibody binds LBP without blocking LPS binding to LBP, or in some embodiments if the antibody prevents LPS binding to CD14. If the monoclonal antibody being tested competes with the monoclonal antibody of the invention, as shown by a decrease in binding by the monoclonal antibody of the invention in standard competition assays for binding to solid phase LBP antigen, then it is likely that the two monoclonal antibodies bind to the same, or a closely related, epitope.

Still another way to determine whether a monoclonal antibody has the specificity of a monoclonal antibody of the invention is to pre-incubate the monoclonal antibody of the invention with LBP with which it is normally reactive, and then add the monoclonal antibody being tested to determine if the monoclonal antibody being tested is inhibited in its ability to bind LBP. If the monoclonal antibody being tested is inhibited then, in all likelihood, it has the same, or functionally equivalent, epitopic specificity as the monoclonal antibody of the invention. Screening of monoclonal antibodies of the invention, can be also carried out utilizing LPS binding assays and determining whether the monoclonal antibody neutralizes LPS binding to LBP and/or CD14, as described further herein.

The immunospecificity of an antibody, its inhibitory capacity, and the attendant affinity the antibody exhibits for the epitope, are defined by the epitope with which the antibody immunoreacts. The epitope specificity is defined at least in part by the amino acid residue sequence of the variable region of the heavy chain of the immunoglobulin the antibody, and in part by the light chain variable region amino acid residue sequence.

By using the monoclonal antibodies of the invention, it is now possible to produce anti-idiotypic antibodies which can be used to screen monoclonal antibodies to identify whether the antibody has the same binding specificity as a monoclonal antibody of the invention and also used for active immunization (Herlyn et al., *Science*, 232:100 (1986)). Such anti-idiotypic antibodies can be produced using well-known hybridoma techniques (Kohler et al., *Nature*, 256:495 (1975)). An anti-idiotypic antibody is an antibody which recognizes unique determinants present on the monoclonal antibody produced by the cell line of interest. These determinants are located in the hypervariable region of the antibody. It is this region which binds to a given epitope and, thus, is responsible for the specificity of the antibody. An anti-idiotypic antibody can be prepared by immunizing an animal with the monoclonal antibody of interest. The immunized animal will recognize and respond to the idiotypic determinants of the immunizing antibody and produce an antibody to these idiotypic determinants. By using the anti-idiotypic antibodies of the immunized animal, which are specific for the monoclonal antibody of the invention produced by a cell line which was used to immunize the second animal, it is now possible to identify other clones with the same idiotype as the antibody of the hybridoma used for immunization. Idiotypic identity between monoclonal antibodies of two cell lines demonstrates that the two monoclonal antibodies are the same with respect to their recognition of the same epitopic determinant. Thus, by using anti-idiotypic antibodies, it is possible to identify other hybridomas expressing monoclonal antibodies having the same epitopic specificity.

It is also possible to use the anti-idiotype technology to produce monoclonal antibodies which mimic an epitope. For example, an anti-idiotypic monoclonal antibody made to a first monoclonal antibody will have a binding domain in the hypervariable region which is the "image" of the epitope bound by the first monoclonal antibody. Thus, the anti-idiotypic monoclonal antibody can be used for immunization, since the anti-idiotype monoclonal antibody binding domain effectively acts as an antigen.

In one preferred embodiment, the invention contemplates a truncated immunoglobulin molecule comprising a Fab fragment derived from a monoclonal antibody of this invention. The Fab fragment, lacking Fc receptor, is soluble, and affords therapeutic advantages in serum half life, and diagnostic advantages in modes of using the soluble Fab fragment. The preparation of a soluble Fab fragment is generally known in the immunological arts and can be accomplished by a variety of methods.

Thus, it is possible for the antibody molecules used herein be an antibody fragment in the form of Fab, Fab', F(ab')$_2$ or F(v) portions of whole antibody molecules as is well known.

While Mabs can be produced by hybridoma culture, the invention is not to be so limited. Also contemplated is the use of Mabs produced by an expressing nucleic acid cloned from a hybridoma of this invention. That is, the nucleic acid expressing the molecules secreted by a hybridoma of this invention can be transferred into another cell line to produce a transformant. The transformant is genotypically distinct from the original hybridoma but is also capable of producing antibody molecules of this invention, including immunologically active fragments of whole antibody molecules, corresponding to those secreted by the hybridoma. See, for example, U.S. Pat. No. 4,642,334 to Reading; PCT Publication No. WO 890099 to Robinson et al.; European Patent Publications No. 0239400 to Winter et al. and No. 0125023 to Cabilly et al. In addition, the literature provides methods for forming chimeric antibodies, humanized antibodies, single chain antibodies and the like variations on a basic immunoreactive antibody fragment. All of these are considered within the scope of the invention insofar as a class and specificity of antibody is disclosed and claimed, regardless of the precise variant structure that one skilled in the art may construct.

A monoclonal antibody useful in practicing the present invention can be produced by initiating a monoclonal hybridoma culture comprising a nutrient medium containing a hybridoma that secretes antibody molecules of the appropriate antigen specificity. The culture is maintained under conditions and for a time period sufficient for the hybridoma to secrete the antibody molecules into the medium. The antibody-containing medium is then collected. The antibody molecules can then be further isolated by well known techniques.

Media useful for the preparation of these compositions are both well known in the art and commercially available and include synthetic culture media, inbred mice and the like. An exemplary synthetic medium is Dulbecco's minimal essential medium (DMEM; Dulbecco et al., *Virol.* 8:396 (1959)) supplemented with 4.5 gm/1 glucose, 20 mm glutamine, and 20% fetal calf serum. An exemplary inbred mouse strain is the Balb/c.

Insofar as hybridoma cell lines can be used to produce a monoclonal antibody of this invention, the hybridoma cell lines themselves are also contemplated by the present invention, particularly those which produce a the preferred antibody of this invention.

C. Immunotherapeutic Methods and Compositions

The monoclonal antibodies can also be used immunotherapeutically for LBP-mediated LPS dependent disease. The term "immunotherapeutically" or "immunotherapy" as used herein in conjunction with the monoclonal antibodies of the invention denotes both prophylactic as well as therapeutic administration. Thus, the monoclonal antibodies can be administered to high-risk patients in order to lessen the likelihood and/or severity of LBP-mediated LPS dependent disease, administered to patients already evidencing active disease, or administered to patients at risk of LPS-induced disease.

1. Therapeutic Compositions

The present invention therefore contemplates therapeutic compositions useful for practicing the therapeutic methods described herein. Therapeutic compositions of the present invention contain a physiologically tolerable carrier together with at least one species of monoclonal antibody as described herein, dissolved or dispersed therein as an active ingredient. In a preferred embodiment, the therapeutic composition is not immunogenic when administered to a human patient for therapeutic purposes, unless that purpose is to induce an immune response, as described elsewhere herein.

As used herein, the terms "pharmaceutically acceptable", "physiologically tolerable" and grammatical variations thereof, as they refer to compositions, carriers, diluents and reagents, are used interchangeably and represent that the materials are capable of administration to or upon a human without the production of undesirable physiological effects such as nausea, dizziness, gastric upset and the like.

The preparation of a pharmacological composition that contains active ingredients dissolved or dispersed therein is well understood in the art. Typically such compositions are prepared as sterile injectables either as liquid solutions or suspensions, aqueous or non-aqueous, however, solid forms suitable for solution, or suspensions, in liquid prior to use can also be prepared. The preparation can also be emulsified.

The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient.

The therapeutic composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like.

Physiologically tolerable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, propylene glycan, polyethylene glycol and other solutes.

Liquid compositions can also contain liquid phases in addition to and to the exclusion of water. Exemplary of such additional liquid phases are glycerin, vegetable oils such as cottonseed oil, organic esters such as ethyl oleate, and water-oil emulsions.

A therapeutic composition contains an anti-LBP monoclonal antibody of the present invention, typically an amount of at least 0.1 weight percent of antibody per weight of total therapeutic composition. A weight percent is a ratio by weight of antibody to total composition. Thus, for example, 0.1 weight percent is 0.1 grams of antibody per 100 grams of total composition.

Preferred therapeutic compositions can further include an effective amount of one or more of the following active ingredients: an antibiotic, a steroid, anti-TNF antibody, anti-CD14 and a TNF antagonist, as discussed herein. Exemplary formulations are given below:

Formulation A

| Ingredient | Dose (mg/ml) |
| --- | --- |
| gentamicin (sulfate) | 40 |
| Anti-LBP (Mab 2B5) | 10 |
| sodium bisulfite USP | 3.2 |
| disodium EDTA USP | 0.1 |
| water for injection q.s.a.d. | 1.0 ml |

Formulation B

| Ingredient | Dose (mg/ml) |
| --- | --- |
| anti-TNF antibody | 10 |
| anti-LBP (Mab 2B5) | 10 |
| sodium bisulfite USP | 3.2 |
| disodium EDTA USP | 0.2 |
| water for injection q.s.a.d. | 1.0 ml |

Formulation C

| Ingredient | Dose (mg/ml) |
| --- | --- |
| gentamicin (sulfate) | 40 |
| anti-TNF antibody | 10 |
| anti-LBP (Mab 2B5) | 10 |
| sodium bisulfite USP | 3.2 |
| disodium EDTA USP | 0.1 |
| water for injection q.s.a.d. | 1.0 ml |

2. Therapeutic Methods

In view of the demonstrated inhibitory ability of the monoclonal antibodies of the present invention, the present disclosure provides for a method for inhibiting LBP-mediated LPS-dependent myeloid cell activation in vitro or in vivo. The method comprises contacting a sample believed to contain myeloid cells expressing CD14, or other receptors responsive to LBP-mediated LPS-induced cell activation with a composition comprising a therapeutically effective amount of a monoclonal antibody of this invention.

For in vivo modalities, the method comprises administering to the patient a therapeutically effective amount of a physiologically tolerable composition containing a monoclonal antibody of the invention. Thus, the present invention describes in one embodiment a method for providing prophylactic immunotherapy to LPS-induced disease in a human comprising administering to the human an immunotherapeutically effective amount of the monoclonal antibody of this invention.

A representative patient for practicing the present immunotherapeutic methods is any human exhibiting symptoms of bacterial, viral or fungal infection, or tissue trauma, immunosuppression or other conditions believed to be caused by LBP-mediated LPS-induced cell activation, and humans at risk of such events. In particular, the methods are directed at patients having conditions associated with cell activation, endotoxemia and/or sepsis, particularly those associated with a transient increase in the blood level of TNF, such as fever, hypotension, neutropenia, leukopenia, thrombocytopenia, shock and multiple organ failure. Patients in need of such treatment include those at risk for or suffering toxemia, such as endotoxemia resulting from a gram-negative bacterial infection, serpent venom poisoning, hepatic failure, and the like. In addition, some patients having a gram-positive bacterial, viral or fungal infection display the symptoms of sepsis and may benefit from a therapeutic method of this invention. Patients particularly able to benefit from the present invention are those suffering infection by *E. coli, Haemophilus influenza B, Neisseria meningitides, staphylococci,* or *pneumococci.* Patients at risk for sepsis include those suffering burns, gunshot wounds, renal or hepatic failure due to chemical poisoning or abuse, and the like.

In one embodiment, the method comprises administering a composition comprising more than one species of monoclonal antibody of this invention, preferably directed to non-competing epitopes of LBP, as to afford increased effectiveness of the immunotherapy.

A therapeutically (immunotherapeutically) effective amount of a monoclonal antibody is a predetermined amount calculated to achieve the desired effect, i.e., to inhibit LBP-mediated LPS dependent myeloid cell activation present in the sample or in the patient, and thereby decrease the amount of detectable cell activation occurring in the sample or patient. In the case of in vivo therapies, an effective amount can be measured by improvements in one or more symptoms associated with myeloid cell activation occurring in the patient, or by comparative in vitro measures of the performance of the patient's myeloid cells in an assay system such as is described herein.

Thus a therapeutically effective amount is typically an amount sufficient to prevent, and preferably reduce by at least about 30 percent, more preferably by at least 50 percent, most preferably by at least 90 percent, a clinically significant increase in the plasma level of TNF as an indicator of LBP-mediated LPS-induced myeloid cell activation. A clinically significant increase in the plasma level of TNF is an increase to at least about 25 pg/ml. Methods for determining the plasma TNF levels are well known in the art, particularly preferred methods being those described herein.

It should be noted that levels of TNF in normal healthy humans or in laboratory animals are estimated to be no more than about 10 pg/ml, a value that is at the limit of detection by the most sensitive assays for TNF. Michie et al., *New Eng. J. Med.* 318:1481–1486 (1988); Mathison et al., *J. Clin. Invest.* 81:1925 (1988) and Waage et al., *Laucet*, 1:355–357 (1987). Following exposure to LPS, the levels of TNF have been shown to rise 10–20 fold to levels of up to 400 pg/ml (vide supra). Recently a good correlation has been shown between serum TNF levels and fatal outcome in infection with gram-negative, LPS-containing meningococcal bacteria. Waage et al., *Lancet*, 1:355–357 (1987). Further in animal models of sepsis with subhuman primates similar increases in TNF were noted and these changes were directly correlated with lethality. Tracey et al., *Nature*, 330:662–664, (1987).

Thus, the dosage ranges for the administration of the monoclonal antibodies of the invention are those large enough to produce the desired effect in which the symptoms of the cell activation are ameliorated or the likelihood of cell activation are decreased. The dosage should not be so large as to cause adverse side effects, such as hyperviscosity syndromes, pulmonary edema, congestive heart failure, and the like. Generally, the dosage will vary with the age, condition, sex and extent of the disease in the patient and can be determined by one of skill in the art.

The dosage can be adjusted by the individual physician in the event of any complication.

A therapeutically effective amount of an antibody of this invention is typically an amount of antibody such that when administered in a physiologically tolerable composition is sufficient to achieve a plasma concentration of from about 0.1 microgram (ug) per milliliter (ml) to about 100 ug/ml, preferably from about 1 ug/ml to about 5 ug/ml, and usually about 5 ug/ml. Stated differently, the dosage can vary from about 0.1 mg/kg to about 300 mg/kg, preferably from about 0.2 mg/kg to about 200 mg/kg, most preferably from about 0.5 mg/kg to about 20 mg/kg, in one or more dose administrations daily, for one or several days.

The monoclonal antibodies of the invention can be administered parenterally by injection or by gradual infusion over time. Although the LBP targeted is typically systemic and therefore most often treated by intravenous administration of therapeutic compositions, other tissues and delivery means are contemplated where there is a likelihood that the tissue targeted contains LBP that might participate in LPS binding to myeloid cells. Thus, monoclonal antibodies of the invention can be administered intravenously, intraperitoneally, intramuscularly, subcutaneously, intracavity, transdermally, and can be delivered by peristaltic means.

The therapeutic compositions containing a monoclonal antibody of this invention are conventionally administered intravenously, as by injection of a unit dose, for example. The term "unit dose" when used in reference to a therapeutic composition of the present invention refers to physically discrete units suitable as unitary dosage for the subject, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, capacity of the subject's system to utilize the active ingredient, and degree of therapeutic effect desired. Precise amounts of active ingredient required to be administered depend on the judgement of the practitioner and are peculiar to each individual. However, suitable dosage ranges for systemic application are disclosed herein and depend on the route of administration. Suitable regimes for administration are also variable, but are typified by an initial administration followed by repeated doses at one or more hour intervals by a subsequent injection or other administration. Alternatively, continuous intravenous infusion sufficient to maintain concentrations in the blood in the ranges specified for in vivo therapies are contemplated.

As an aid to the administration of effective amounts of a monoclonal antibody, a diagnostic method for detecting a monoclonal antibody in the subject's blood is useful to characterize the fate of the administered therapeutic composition.

The invention also relates to a method for preparing a medicament or pharmaceutical composition comprising the monoclonal antibodies of the invention, the medicament being used for immunotherapy of LBP-mediated LPS-induced activation of myeloid cells.

Patients at risk for or exhibiting the symptoms of sepsis are capable of benefiting from the administration of therapeutic modalities known in the art to prevent or ameliorate those symptoms. Thus, the present invention also contemplates administering a therapeutically effective amount of an anti-LBP antibody substantially simultaneously with therapeutic administration of a modality known to prevent or treat the symptoms of sepsis. For instance, intervention in the role of TNF in sepsis, either directly or indirectly, such as by use of an anti-TNF antibody and/or a TNF antagonist, can prevent or ameliorate the symptoms of sepsis. Particularly preferred is the use of an anti-TNF antibody as an active ingredient, such as a monoclonal antibody having an immunologic specificity for TNF corresponding to that described by [Tracey et al., Nature, 330:662–664 (1987)].

Similarly, a therapeutic method of this invention can further include substantially simultaneous treatment with a steroid, such as cortisol, hydrocortisone and the like.

A patient exhibiting the symptoms of sepsis is usually treated with an antibiotic, typically an aminoglycoside such as gentamicin or a beta-lactam such as penicillin, cephalosporin and the like. Thus, a preferred therapeutic method includes administering a therapeutically effective amount of an anti-LBP antibody as described herein, substantially simultaneously with administering a bactericidal amount of an antibiotic. The phrase "bactericidal amount" is used herein to mean an amount sufficient to achieve a bacteria-killing blood concentration in the patient receiving the treatment. The bactericidal amount of antibiotics generally recognized as safe for administration to humans is an amount well known in the art and varies, as is also well known, with the antibiotic and the type of bacterial infection being treated.

In preferred embodiments, administration of an anti-LBP antibody as described herein occurs within about 48 hours, preferably within about 12–36 hours, more preferably within about 2–8 hours and most preferably substantially concurrently with administration of the antibiotic.

Antibiotics useful in practicing the present invention include those antibiotic, antibacterial and antiseptic agents having formulations described in the Physicians' Desk Reference, Huff, B. B. ed., Medical Economics Company, Inc., Oradell, N.J. (1989).

In another embodiment, the present invention contemplates administering a therapeutically effective amount of CD14, preferably a soluble portion thereof that binds LPS-LBP complexes, alone or in subcombination or combination with a therapeutically effective amount of an anti-LBP antibody, an anti-CD14 antibody and an antibiotic. The CDNA coding for CD14 and its deduced amino acid residue sequence are well known in the art. See Goyert et al, Science, 239:497–500 (1988), Ferrero et al., Nuc. Acids Res., 16:4173 (1988), and Bazil et al., Eur. J. Immunol., 16:1583–1589 (1986).

D. Diagnostic Assay Methods

The present invention contemplates various assay methods for determining the presence, and preferably amount, of LBP in a sample such as a biological fluid or tissue sample using a monoclonal antibody of this invention as an immunochemical reagent to form an immunoreaction product whose amount relates, either directly or indirectly, to the amount of LBP in the sample.

Those skilled in the art will understand that there are numerous well known clinical diagnostic chemistry procedures in which an immunochemical reagent of this invention can be used to form an immunoreaction product whose amount relates to the amount of LBP present in a body sample. Thus, while exemplary assay methods are described herein, the invention is not so limited.

Various heterogenous and homogeneous protocols, either competitive or noncompetitive, can be employed in performing an assay method of this invention. Examples of types of immunoassays which can utilize monoclonal antibodies of the invention are competitive and non-competitive immunoassays in either a direct or indirect format.

Examples of such immunoassays are the radioimmunoassay (RIA) and the sandwich (immunometric) assay. Detection of the antigens using the monoclonal antibodies of the invention can be done utilizing immunoassays which are run in either the forward, reverse, or simultaneous modes, including immunohistochemical assays on physiological samples. Those of skill in the art will know, or can readily discern, other immunoassay formats without undue experimentation.

The monoclonal antibodies of the invention can be bound to many different carriers and used to detect the presence of LBP. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding monoclonal antibodies, or will be able to ascertain such, using routine experimentation.

There are many different labels and methods of labeling known to those of ordinary skill in the art. Examples of the types of labels which can be used in the present invention include enzymes, radioisotopes, fluorescent compounds, colloidal metals, chemiluminescent compounds, and bioluminescent compounds. Those of ordinary skill in the art will know of other suitable labels for binding to the monoclonal antibodies of the invention, or will be able to ascertain such, using routine experimentation. Furthermore, the binding of these labels to the monoclonal antibodies of the invention can be done using standard techniques common to those of ordinary skill in the art.

For purposes of the invention, LBP may be detected by the monoclonal antibodies of the invention when present in samples of biological fluids and tissues. Any sample containing a detectable amount of LBP can be used. A sample can be a liquid such as urine, saliva, cerebrospinal fluid, blood, serum and the like, or a solid or semi-solid such as tissues, feces, and the like, or, alternatively, a solid tissue such as those commonly used in histological diagnosis.

Another labeling technique which may result in greater sensitivity consists of coupling the antibodies to low molecular weight haptens. These haptens can then be specifically detected by means of a second reaction. For example, it is common to use haptens such as biotin, which reacts with avidin, or dinitrophenol, pyridoxal, or fluorescein, which can react with specific anti-hapten antibodies.

The monoclonal antibodies of the invention are suited for use in vitro, for example, in immunoassays in which they can be utilized in liquid phase or bound to a solid phase carrier for the detection of LBP in samples, as described above. The monoclonal antibodies in these immunoassays can be detectably labeled in various ways for in vitro use.

A particularly preferred assay format is the use of capture and detection antibodies, one from each competition group, i.e., the 1E8 group and the 2B5 group, as described further herein. This "sandwich" format is well known in the art, and is described in the Examples.

In using the monoclonal antibodies of the invention for the in vivo detection of antigen, the detectably labeled monoclonal antibody is given in a dose which is diagnostically effective. The term "diagnostically effective" means that the amount of detectably labeled monoclonal antibody is administered in sufficient quantity to enable detection of the site having the LBP antigen for which the monoclonal anti-bodies are specific.

The concentration of detectably labeled monoclonal antibody which is administered should be sufficient such that the binding to LBP is detectable compared to the background. Further, it is desirable that the detectably labeled monoclonal antibody be rapidly cleared from the circulatory system in order to give the best target-to-background signal ratio.

As a rule, the dosage of detectably labeled monoclonal antibody for in vivo diagnosis will vary depending on such factors as age, sex, and extent of disease of the individual. The dosage of monoclonal antibody can vary from about 0.01 mg/m$^2$ to about 500 mg/m$^2$, preferably 0.1 mg/m$^2$ to about 200 mg/m$^2$, most preferably about 0.1 mg/m$^2$ to about 10 mg/m$^2$. Such dosages may vary, for example, depending on whether multiple injections are given, tissue, and other factors known to those of skill in the art.

For in vivo diagnostic imaging, the type of detection instrument available is a major factor in selecting a given radioisotope. The radioisotope chosen must have a type of decay which is detectable for a given type of instrument. Still another important factor in selecting a radioisotope for in vivo diagnosis is that the half-life of the radioisotope be long enough so that it is still detectable at the time of maximum uptake by the target, but short enough so that deleterious radiation with respect to the host is minimized. Ideally, a radioisotope used for in vivo imaging will lack a particle emission, but produce a large number of photons in the 140–250 keV range, which may be readily detected by conventional gamma cameras.

For in vivo diagnosis radioisotopes may be bound to immunoglobulin either directly or indirectly by using an intermediate functional group. Intermediate functional groups which often are used to bind radioisotopes which exist as metallic ions to immunoglobulins are the bifunctional chelating agents such as diethylenetriaminepentacetic acid (DTPA) and ethylenediaminetetraacetic acid (EDTA) and similar molecules. Typical examples of metallic ions which can be bound to the monoclonal antibodies of the invention are $^{111}$In, $^{97}$Ru, $^{67}$Ga, $^{68}$Ga, $^{72}$As, $^{89}$Zr, and $^{201}$Tl.

The monoclonal antibodies of the invention can also be labeled with a paramagnetic isotope for purposes of in vivo diagnosis, as in magnetic resonance imaging (MRI) or electron spin resonance (ESR). In general, any conventional method for visualizing diagnostic imaging can be utilized. Usually gamma and positron emitting radioisotopes are used for camera imaging and paramagnetic isotopes for MRI. Elements which are particularly useful in such techniques include $^{157}$Gd, $^{55}$Mn, $^{162}$Dy, $^{52}$Cr, and $^{56}$Fe.

The monoclonal antibodies of the invention can be used in vitro and in vivo to monitor the course of LBP-mediated LPS-dependent disease therapy. Thus, for example, by measuring the increase or decrease in the concentration of LBP present in the body or in various body fluids, it would be possible to determine whether a particular therapeutic regimen aimed at ameliorating the LBP-mediated disease is effective.

E. Diagnostic Systems

The present invention also describes a diagnostic system, preferably in kit form, for assaying for the presence of LBP in a sample according to the diagnostic methods described herein. A diagnostic system includes, in an amount sufficient to perform at least one assay, a subject monoclonal antibody, as a separately packaged reagent.

In another embodiment, a diagnostic system is contemplated for assaying for the presence of an anti-LBP monoclonal antibody in a body fluid sample such as for monitoring the fate of therapeutically administered antibody. The system includes, in an amount sufficient for at least one assay, a subject antibody as a control reagent, and preferably a preselected amount of LBP antigen, each as separately packaged immunochemical reagents.

Instructions for use of the packaged reagent are also typically included.

"Instructions for use" typically include a tangible expression describing the reagent concentration or at least one assay method parameter such as the relative amounts of reagent and sample to be admixed, maintenance time periods for reagent/sample admixtures, temperature, buffer conditions and the like.

In embodiments for detecting LBP in a body sample, a diagnostic system of the present invention can include a label or indicating means capable of signaling the formation of an immunocomplex containing a monoclonal antibody of the present invention.

The word "complex" as used herein refers to the product of a specific binding reaction such as an antibody-antigen reaction. Exemplary complexes are immunoreaction products.

As used herein, the terms "label" and "indicating means" in their various grammatical forms refer to single atoms and molecules that are either directly or indirectly involved in the production of a detectable signal to indicate the presence of a complex. Any label or indicating means can be linked to or incorporated in an expressed protein, polypeptide, or antibody molecule that is part of an antibody or monoclonal antibody composition of the present invention, or used separately, and those atoms or molecules can be used alone or in conjunction with additional reagents. Such labels are themselves well-known in clinical diagnostic chemistry and constitute a part of this invention only insofar as they are utilized with otherwise novel proteins methods and/or systems.

The labeling means can be a fluorescent labeling agent that chemically binds to antibodies or antigens without denaturing them to form a fluorochrome (dye) that is a useful immunofluorescent tracer. Suitable fluorescent labeling agents are fluorochromes such as fluorescein isocyanate (FIC), fluorescein isothiocyante (FITC), 5-dimethylamine-1-naphthalenesulfonyl chloride (DANSC), tetramethylrhodamine isothiocyanate (TRITC), lissamine, rhodamine 8200 sulphonyl chloride (RB 200 SC) and the like. A description of immunofluorescence analysis techniques is found in DeLuca, "Immunofluorescence Analysis", in *Antibody As a Tool*, Marchalonis et al., eds., John Wiley & Sons, Ltd., pp. 189–231 (1982), which is incorporated herein by reference.

In preferred embodiments, the indicating group is an enzyme, such as horseradish peroxidase (HRP), glucose oxidase, or the like. In such cases where the principal indicating group is an enzyme such as HRP or glucose oxidase, additional reagents are required to visualize the fact that a receptor-ligand complex (immunoreactant) has formed. Such additional reagents for HRP include hydrogen peroxide and an oxidation dye precursor such as diaminobenzidine. An additional reagent useful with glucose oxidase is 2,2'-amino-di-(3-ethyl-benzthiazoline-G-sulfonic acid) (ABTS).

Radioactive elements are also useful labeling agents and are used illustratively herein. An exemplary radiolabeling agent is a radioactive element that produces gamma ray emissions. Elements which themselves emit gamma rays, such as $^{124}$I, $^{125}$I, $^{128}$I, $^{132}$I and $^{51}$Cr represent one class of gamma ray emission-producing radioactive element indicating groups. Particularly preferred is $^{125}$I. Another group of useful labeling means are those elements such as $^{11}$C, $^{18}$F, $^{15}$O and $^{13}$N which themselves emit positrons. The positrons so emitted produce gamma rays upon encounters with electrons present in the animal's body. Also useful is a beta emitter, such $^{111}$ indium of $^3$H.

The linking or labels, i.e., labeling of, polypeptides and proteins is well known in the art. For instance, antibody molecules produced by a hybridoma can be labeled by metabolic incorporation of radioisotope-containing amino acids provided as a component in the culture medium. See, for example, Galtre et al., *Meth. Enzymol.*, 73:3–46 (1981). The techniques of protein conjugation or coupling through activated functional groups are particularly applicable. See, for example, Aurameas et al., *Scand. J. Immunol.*, Vol. 8 Suppl. 7:7–23 (1978), Rodwell et al., *Biotech.*, 3:889–894 (1984), and U.S. Pat. No. 4,493,795.

The diagnostic systems can also include, preferably as a separate package, a specific binding agent. A "specific binding agent" is a molecular entity capable of selectively binding a reagent species of the present invention or a complex containing such a species, but is not itself a polypeptide or antibody molecule composition of the present invention. Exemplary specific binding agents are second antibody molecules, complement proteins or fragments thereof, *S. aureus* protein A, and the like. Preferably the specific binding agent binds the reagent species when that species is present as part of a complex.

In preferred embodiments, the specific binding agent is labeled. However, when the diagnostic system includes a specific binding agent that is not labeled, the agent is typically used as an amplifying means or reagent. In these embodiments, the labeled specific binding agent is capable of specifically binding the amplifying means when the amplifying means is bound to a reagent species-containing complex.

The diagnostic kits of the present invention can be used in an "ELISA" format to detect the quantity of an LBP in a vascular fluid sample such as blood, serum, or plasma. "ELISA" refers to an enzyme-linked immunosorbent assay that employs an antibody or antigen bound to a solid phase and an enzyme-antigen or enzyme-antibody conjugate to detect and quantify the amount of an antigen present in a sample. A description of the ELISA technique is found in Chapter 22 of the 4th Edition of *Basic and Clinical Immunology* by D. P. Sites et al., published by Lange Medical Publications of Los Altos, Calif. in 1982 and in U.S. Pat. Nos. 3,654,090; 3,850,752; and 4,016,043, which are all incorporated herein by reference.

Thus, in some embodiments, a monoclonal antibody of the present invention can be affixed to a solid matrix to form a solid support that comprises a package in the subject diagnostic systems.

A reagent is typically affixed to a solid matrix by adsorption from an aqueous medium although other modes of affixation applicable to proteins and polypeptides well known to those skilled in the art, can be used.

Useful solid matrices are also well known in the art. Such materials are water insoluble and include the cross-linked dextran available under the trademark SEPHADEX from Pharmacia Fine Chemicals (Piscataway, N.J.); agarose; beads of polystyrene beads about 1 micron to about 5 millimeters in diameter available from Abbott Laboratories of North Chicago, Ill.; polyvinyl chloride, polystyrene, cross-linked polyacrylamide, nitrocellulose- or nylon-based webs such as sheets, strips or paddles; or tubes, plates or the wells of a microtiter plate such as those made from polystyrene or polyvinylchloride.

The reagent species, labeled specific binding agent or amplifying reagent of any diagnostic system described herein can be provided in solution, as a liquid dispersion or as a substantially dry power, e.g., in lyophilized form. Where the indicating means is an enzyme, the enzyme's substrate can also be provided in a separate package of a system. A solid support such as the before-described microtiter plate and one or more buffers can also be included as separately packaged elements in this diagnostic assay system.

The packaging materials discussed herein in relation to diagnostic systems are those customarily utilized in diagnostic systems.

The term "package" refers to a solid matrix or material such as glass, plastic (e.g., polyethylene, polypropylene and polycarbonate), paper, foil and the like capable of holding within fixed limits a diagnostic reagent such as a monoclonal antibody of the present invention. Thus, for example, a package can be a bottle, vial, plastic and plastic-foil laminated envelope or the like container used to contain a contemplated diagnostic reagent or it can be a microtiter plate well to which microgram quantities of a contemplated diagnostic reagent have been operatively affixed, i.e., linked so as to be capable of being immunologically bound by an antibody or polypeptide to be detected.

The materials for use in the assay of the invention are ideally suited for the preparation of a kit. Such a kit may comprise a carrier means being compartmentalized to receive in close confinement one or more container means such as vials, tubes, and the like, each of the container means comprising one of the separate elements to be used in the method. For example, one of the container means may comprise a monoclonal antibody of the invention which is, or can be, detectably labelled. The kit may also have containers containing any of the other above-recited immunochemical reagents used to practice the diagnostic methods.

As used herein, "pg" means picogram, "ng" means nanogram, "ug" means microgram, "mg" means milligram, "ul" means microliter, "ml" means milliliter, "l" means liter.

EXAMPLES

The following examples relating to this invention are illustrative and should not, of course, be construed as specifically limiting the invention. Moreover, such variations of the invention, now known or later developed, which would be within the purview of one skilled in the art are to be considered to fall within the scope of the present invention hereinafter claimed.

1. Preparation of Anti-LBP Monoclonal Antibodies

Monoclonal antibodies to LBP, lipopolysaccharide binding protein, were generated by somatic cell fusion between spleen cells from BAL8/c mice immunized with purified human LBP prepared as described by Schumann et al., *Science*, 249:1429–1431 (1990), the disclosure of which is hereby incorporated by reference, and the mouse myeloma call line X63.Ag8.653. Anti-LBP specific hybridomas were screened by enzyme immunoassay (EIA) against purified LBP and subcloned by limiting dilution. Anti-LBP specificity of the antibodies was confirmed by immunoprecipitation, Western blot and competition experiments.

Using these techniques and as shown by the experimental results presented in Examples below, the monoclonal antibody designated 8C9 was found to be specific for denatured LBP and did not recognize native LBP. The monoclonal antibodies, 2B5 and 18G4, recognized overlapping epitopes on LBP; the monoclonal antibodies, 1E8 and 8F5, recognized unique LBP epitopes. None of the mAb were capable of blocking LBP binding of LPS (bacterial lipopolysaccharide); however, the binding of 1E8 and SF5 to LBP was slightly reduced after LPS binding. The remaining anti-LBP monoclonal antibodies further characterized as shown in the Examples below included 4D7, 5C5, 6B6, and 24B7. All the mAb were determined to be of the IgG1 subclass.

2. Characterization of the Binding Specificity of Anti-LBP Monoclonal Antibodies and Their Use in Inhibiting LBP-Mediated Cell Activation LPS derived from Gram-negative bacteria is a potent stimulator of inflammation in many animal species. A wide variety of different types of cells respond to LPS, including macrophages, polymorphonuclear leukocytes and endothelial cells as described by Rietschel et al., *Scientific American*, 267:54–61 (1992). In human beings with bacteremia caused by Gram negative bacteria, these reactions can cause a syndrome of profound shock and multi-organ failure. The nature of a cellular LPS receptor, capable of binding LPS and triggering cellular responses has been controversial. See, Kirkland et al., *J. Biol. Chem.*, 265:9520–9525 (1990); Lei et al., *J. Immunol.*, 141:996–1005 (1988); and Golenbock et al., *Infect. Immunol.*, 58:4069–4075 (1990). Though several candidate LPS receptors have been proposed, until recently none of them have been conclusively proven to bind LPS and transmit signals to the cell. A recent major advance in the understanding of the mammalian response to LPS has been the observation that the cell surface molecule, CD14 (Ferrero et al., *J. Immunol.*, 145:331–336 (1990)), plays a role in recognition of LPS, in the presence of LBP, as described by Tobias et al., *J. Biol. Chem.*, 264:10867–10871 (1989).

CD14, a macrophage/polymorphonuclear leukocyte differentiation antigen, has been reported to bind LPS in the presence of LBP. See, Wright et al., *Science*, 249:1431–1433 (1990); Couturier et al., *J. Immunol.*, 147:1899–1904 (1991); Heumann et al., *J. Immunol.*, 148:3505–3511 (1992); Kitchens et al., *J. Exp. Med.*, 176:485–494 (1992) and Lee et al., *J. Exp. Med.*, 175:1697–1705 (1992). LPS binding to CD14 has also been shown in a variety of assay systems to activate cellular responses. The anti-LBP monoclonal antibodies of this invention have now been shown to bind LBP at epitopes distinct from the LPS binding sites thereby not inhibiting the formation of LBP:LPS complexes. While not inhibiting the formation of LBP:LPS complexes, the anti-LBP antibodies to both inhibit the transfer of LPS from the LBP:LPS complex to CD14 and the consequent cellular activation of CD14-expressing cells. The Examples below detail the experimental approaches used in characterizing the properties of the anti-LBP monoclonal antibodies of this invention.

A. Binding of LPS by CD14-Expressing CHO Cells

In order to determine the effect of anti-LBP monoclonal antibodies on the transfer of LPS from a LBP:LPS complex to CD14, binding assays were performed to show that LPS was bound by the CD14 receptor on the surface of CHO cells.

For the assay, CHO cells were first transfected with an expression vector containing cDNA encoding human CD14. CD14 cDNA was cloned in the expression vector pRc/RSV (Invitrogen, San Diego, Calif.) as previously described by Lee et al., *J. Exp. Med.*, 175:1697–1705 (1992). In the experiments, pRc/RSV without the CD14 cDNA was used as a control. CHO K1cells were transfected with 10 micrograms (ug) plasmid DNA using the lipofection reagent N-[1-(2,3-Dioleoyloxy)propyl]-N,N,N-trimethylammonium methyl sulfate according to the manufacturer's instructions (Boehringer Mannheirm, Indianapolis, Ind.). G418 (1 mg/ml) was used to select stable transfectants. CD14 expression was detected by flow microfluorometry using FITC-MY-4 (Coulter, Hialeah, Fla.). Cells expressing CD14 were selected by fluorescence-activated cell sorting with FITC-MY-4 and frozen stocks made. CD14-expressing CHO cells were started from frozen stocks every 6 weeks to minimize variability in expression of CD14.

Other cultured cells lines, such as THP cells, were used in the assays as described herein. THP-1 cells were induced to express CD14 by treatment for 48 hours with 0.1 uM 1,23-dihydroxy vitamin $D_3$ (Biomol Research Laboratories, Plymouth Meeting, Pa.).

Cell surface CD14 expression was measured using $^{125}$I labeled Fab fragments of an anti-human CD14 monoclonal antibody. Fab fragments of the CD14-specific monoclonal antibody, 28C5, were prepared using immobilized papain according to the manufacturer's instructions (Pierce Immunopure Fab preparation kit, Pierce Chemical Co., Rockford, Ill.) and iodinated using chloramine T. Specific activities were typically $1\times10^{18}$ cpm per mol Fab and the Fab fragments were stable for 2–3 weeks at 4C. Cells, $5\times10^4$, were pelleted into microfuge tubes and resuspended in 50 ul FHE-RPMI buffer (10% fetal calf serum, 25 mM HEPES, 1 mM EDTA in RPMI-1640) containing the $^{125}$I-Fab at $1\times10^{-9}$ to $80\times10^{-9}$ M in ten increments with or without $6.7\times10^{-6}$ M intact, unlabeled 28C5 to block specific binding sites. All reactions were run at least in duplicate. After incubation with agitation at 4C for 1 hour the cells were layered on top of 200 uL 10% sucrose in water, quickly pelleted and the tube frozen in liquid $N_2$. The tubes were then cut to separate the bound from free counts, both were quantitated in a gamma counter, and the data analyzed using a Scatchard plot to determine the number of $^{125}$I-Fab binding sites per cell as well as the dissociation constant. Non-specific binding was generally less than 5% of the total binding.

The CD14-expressing CHO cells expressed $4.4\times10^5$ 28C5 $^{125}$I-Fab binding sites per cell with a Kd of $2.5\times10^{-9}$ M. The vector only transfected cells had no detectable expression of CD14. THP-1 cells induced with vitamin D3 for 48 hours expressed $6.8\times10^5$ 28C5 $^{125}$I-Fab binding sites per cell with a Kd of $4.8\times10^{-9}$ M.

For use in the assays, LPS from E. coli LCD25, a K12 derivative with Ra or Rb core structure, was biosynthetically labeled with $^3$H-acetate as previously described by Munford et al., J. Immunol. Methods, 148:115–120 (1992). The LPS, with a specific activity of $6\times10^6$ dpm/ug, was a gift from Dr. Robert Munford (University of Texas Southwestern Medical School, Dallas, Tex.). The molecular mass of the LPS monomer was assumed to be 4000 daltons, in accordance with previous estimates. Human serum was obtained from Gemini Bioproducts, (Calabasas, Calif.).

The $^3$H-labeled LPS was aliquoted and stored at −70 degrees Centigrade (−70C). Fresh aliquots were thawed, diluted in binding buffer and sonicated as described for each assay as described by Kitchens et al., J. Exp. Med., 176:485–494 (1992). In preliminary experiments, it was determined that most of the LPS bound at 22C or higher in physiologic media could not be released by phosphatidylinositol-specific phospholipase C (PI-PLC) treatment, indicating that it was no longer associated with CD14.

The following conditions were found to minimize transfer of LPS from CD14 to other structures. The binding buffer consisted of 0.15 M NaCl, 20 mM HEPES, 1 mM EDTA, 0.3 mg/ml BSA and 0.05% sodium azide, pH 7.4. The stably transfected CHO cells prepared above were harvested by treatment with 1 mM EDTA, 10 mM HEPES, 0.15 M NaCl, washed twice, and resuspended in binding buffer at $1\times10^7$ cells per ml. For assessment of binding, $2\times10^5$ cells were incubated in a total volume of 50 ml in a 1.7 ml microfuge tube for 30 minutes at 10C with $^3$H-LPS with human serum or purified LBP. Then 500 microliters (ul) of binding buffer (at 4C) were added, the cells centrifuged, and the supernate removed. Fifty ul of binding buffer were added, and the cells incubated at 10C for another 30 minutes. The second incubation was done to minimize nonspecific binding. The cells were washed with 500 ul of binding buffer, pelleted, solubilized with 50 ul 2% SDS and counted in a scintillation counter. All assays were done in triplicate.

The binding of LPS by CD14-expressing CHO cells and vector transfected control cells (RSV-CHO) is shown in FIG. 1. CD14-expressing CHO cells bound LPS in a concentration-dependent manner in the presence of serum. RSV-CHO cells bound 50 fold lower amounts of LPS than did CD14-expressing CHO cells regardless of whether or not serum was present.

To confirm that the CD14 molecule was responsible for the observed LPS binding, the ability of anti-CD14 mAb to inhibit binding was tested. Six monoclonal antibodies, mAb, specific for CD14 were tested for their ability to inhibit CD14-expressing CHO cell binding of LPS. Monoclonal antibodies to human CD14 were generated by somatic cell fusion between spleen cells from BALB/c mice immunized with purified human recombinant CD14 and the mouse myeloma cell line X63.Ag8.653. The CD14-specific monoclonal antibodies, designated 28C5, 18E12 and 5G3, are three IgG1 mAb which were identified by screening against CD14 in an EIA. Binding to native CD14 was confirmed by flow microfluorometry on CD14$^+$ cells and immunoprecipitation of biosynthetically labeled CD14. 28C5, 18E12 and 5G3 recognized cell associated and soluble CD14. Competition studies indicated that these mAb bound to three distinct CD14 epitopes. 60 bca (a subclone of 670 bd) and 121n, two IgG1 monoclonal antibodies specific for CD14 as described by Ashmun et al., Blood, 69:886–892 (1987) were also used in some assays. MY-4 (IgG2a) was obtained from Coulter Immunology (Hialeah, Fla.). Although all six CD14-specific monoclonal antibodies bound CD14-expressing CHO cells in a fluorescence assay, only three inhibited the binding of LPS. The mAb tested inhibited binding completely or not at all.

These experiments confirm previous reports that cells expressing CD14 bind LPS, in the presence of serum or LBP. LPS binding to the cells required both CD14 and LBP. The requirement for CD14 was demonstrated in two ways. First, CD14 expressing CHO cells bound 50-fold more LPS than vector-transfected cells. In addition, LPS binding to CD14-expressing CHO cells was blocked by anti-CD14 mAb. The observation that only a subset of anti-CD14 mAb (all of which are capable of recognizing CD14 on CHO cells) blocked LPS binding indicates that the LBP-dependent binding of LPS to CD14 occurred within a specific LPS binding site on the CD14 molecule. Previously published studies (Lee et al., J. Exp. Med., 175:1697–1705 (1992)) indicated that CD14 expressed on 70Z/3 cells enhances LPS binding in the presence of serum. Furthermore, anti-CD14 mAb have been shown to inhibit the binding of LPS by monocytes and macrophage-like cell lines. These observations indicate that CD14 is a critical molecule for the binding of LPS by many types of cells.

Figure 2:
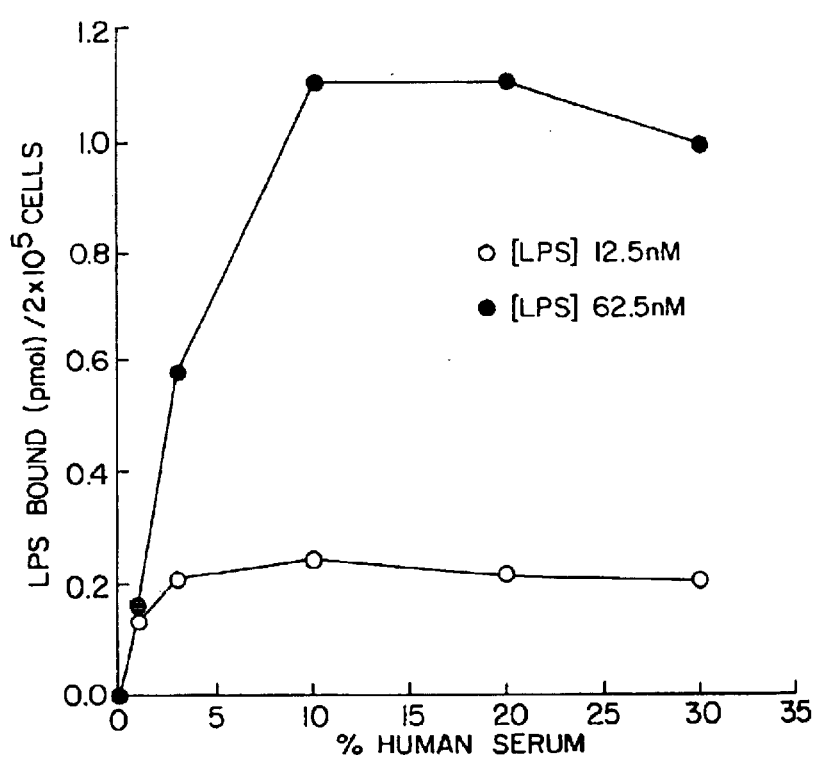
FIG. 2 illustrates LPS binding in pMol at different concentrations of serum ranging from 0 to 30%. The binding was done at 10C as described in Example 2B. The open and closed circles respectively represent assay results in the presence of LPS at 12.5 nM and 62.5 nM. The data points represent the means determinations; the standard deviations are smaller than the symbols.

B. Determination of the Concentration of Human Serum Containing LBP for Maximal Binding The concentration of human serum required for maximal binding of LPS to CD14 was then investigated. The cell binding of CD14-expressing CHO to LPS at two concentrations of LPS as a function of the concentration of human serum ranging from 0 to 30% is shown in FIG. 2. The assays were performed as described in Example 2A. The data is expressed as the amount of LPS bound in picomoles (pMol) against increasing amounts of human serum in the presence of either 12.5 or 62.5 nM LPS. At an LPS concentration of 62.5 nM, 10% human serum was sufficient for maximal binding. At a 5 fold lower concentration of LPS, 3% serum was sufficient for maximal binding.

The amount of LBP in serum was determined using an EIA. Goat polyclonal antiserum was raised against recombinant human LBP (rh-LBP) expressed in a baculovirus/SF-9 cell system. Goat anti-(rh-LBP) immunoglobulin was purified from the serum using DEAE-cellulose chromatography and a portion biotinylated using biotinamidocaproate N-hydroxysuccinimide ester according to manufacturer's directions (Sigma, St. Louis, Mo.). The goat anti-rh-LBP IgG was used to coat a microtiter plate and the plate was blocked with non-fat dry milk dissolved' in phosphate buffered saline (PBS). Samples and standards were then added (in triplicate) and incubated in the plate for at least 1 hour at 37C. After thorough washing the biotinylated goat anti-rh-LBP IgG was then added and allowed to bind for an additional hour. Finally, streptavidin-peroxidase conjugate was allowed to bind to the biotinylated antibody and quantitated with ortho-phenylene diamine. This assay readily detected 10 ng/ml human LBP.

C. Determination of the Effect of Purified LBP and Anti-LBP Monoclonal Antibodies on the Binding of LPS to CD14

The role of LBP in the serum-dependent binding was then determined with the following two approaches: 1) substitution of purified LBP for serum and 2) inhibition of the serum effect with anti-LBP mAbs. The assays were performed as described in Example 2A with the changes specified below. For the assay where LPS binding to CD14 in the presence of purified LBP, CD14-expressing CHO cells prepared in Example 2A were incubated with 37.5 nM $^3$H-LPS at 10C. The binding assays were done with purified rabbit LBP.

Figure 3:
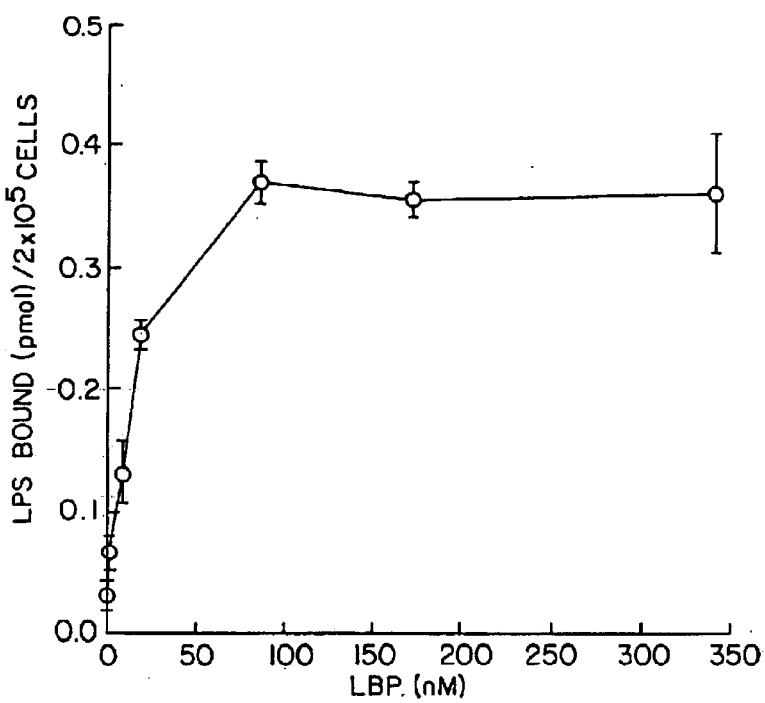
FIG. 3 illustrates LPS binding in pMol/2×10$^5$ cells at different concentrations of LBP ranging from 0 to 350 nM of LBP. CD14-expressing CHO cells were incubated with 37.5 nM $^3$H-LPS at 10C. The binding assays were done with purified rabbit LBP as described in Example 2C.

FIG. 3 shows $^3$H-LPS binding by CHO cells expressing CD14 as a function of the concentration of purified LBP. LBP at a concentration of 100 nM (6 ug/ml) was sufficient to catalyze the maximal binding of 37.5 nM (150 ng/ml) $^3$H-LPS.

To determine if, and through what mechanism, the anti-LBP monoclonal antibodies of this invention inhibited the transfer of LPS to CD14, two separate assays were performed. For the first assay, separate preparations of anti-LBP monoclonal antibodies (mAb) were first preincubated with serum. For this assay, 10 ug/ml of each of the mAbs, 8C9, 1E8, 8F5, 2B5 and 18G4 were separately added to 10% human serum in buffer as described in Example 2A and incubated for 30 minutes at 10C. Following this preincubation, 37.5 nM $^3$H-LPS was then added and incubated for an additional 30 minutes at 10C. CD14-expressing CHO cells, prepared in Example 2A, were then added at a -concentration of 2×10$^5$. The remainder of the assay was then performed as described in Example 2A.

For the other assay, LPS was first preincubated with serum prior to the addition of antibodies. For this approach, 37.5 nM $^3$H-LPS was first added to 10% human serum in buffer and incubated for 30 minutes at 10C, followed by the separate addition of 10 ug/ml of each of the anti-LBP antibodies listed above. The admixture was maintained for an additional 30 minutes. The remainder of the assay was performed as described above. The results shown below in Table 1 are derived from samples containing 10% human serum. In the absence of serum, 0.063 pMol of $^3$H-LPS was bound. The means of the separate assays are shown; the standard deviation for each mean was always less than 10% of the mean. The data is presented as the amount of LPS bound/2×10$^5$ cells. The percent of control binding is also shown.

TABLE 1

| Preincubation | mAb | LPS bound/ 2 × 10$^5$ cells pmol | Control % |
|---|---|---|---|
| mAb/serum | None | 1.32 | 100 |
|  | 8C9 | 1.34 | 102 |
|  | 1E8 | 0.1 | 7.6 |
|  | 8F5 | 1.25 | 95 |
|  | 2B5 | 0.01 | 0.8 |
|  | 18G4 | 0.07 | 5 |
| LPS/serum | None | 0.88 | 100 |
|  | 8C9 | 0.82 | 93 |
|  | 1E8 | 0.04 | 4.5 |
|  | 8F5 | 0.81 | 92 |
|  | 2B5 | 0.04 | 4.5 |
|  | 18G4 | 0.05 | 5.6 |

Three monoclonal antibodies to LBP, 1E8, 2B5 and 18G4, inhibited the binding of LPS by CD14-expressing CHO cells as shown in Table 1 in one approach where the anti-LBP mAb was added either before the LPS, or in the other approach where the LPS was added to the serum, allowed to bind to the LBP, and then the mAb added. The anti-LBP mAb blocked the transfer of LPS from LBP to CD14 since they were equally effective whether or not the LBP was allowed to bind LPS before the addition of antibody. Therefore, serum-dependent binding of LPS to CD14-expressing CHO was completely dependent on LBP. Furthermore, none of these mAb were capable of inhibiting LBP binding of LPS as demonstrated by the capture assays shown in the Examples below. In those assays, the binding site of LPS to LBP was distinct from the LBP epitopes to which the anti-LBP antibodies bound. The above results indicate that LBP has both an LPS binding domain and another domain that is required for the transfer of LPS to CD14.

Bactericidal/permeability-increasing protein, another LPS binding protein, with significant structural similarity to LBP, also appears to have at least two functionally significant domains as well as described by Gazzano-Santoro et al., *Infect. Immunol.*, 60:4754–4761 (1992). The ability of some anti-LBP mAb to completely inhibit CD14-expressing CHO binding of LPS indicates that LBP is absolutely required for LPS binding. Two of the anti-LBP mAb have been shown to be specific for LBP and not recognize other LPS-binding proteins in serum as described by Pugin et al., *Proc. Natl. Acad. Sci. USA*, 90:2744–2748 (1993). Therefore, other LPS binding proteins in serum such as high density lipoprotein (Ulevitch et al., *J. Clin. Invest.*, 67:827–837 (1981)), albumin (Takayama et al., *J. Biol. Chem.*, 265:14023–14029 (1990)) and septin (Wright et al., *J. Exp. Med.*, 176:719–727 (1992)), are not sufficient to promote CD14 binding to LPS. CD14-depleted serum was as effective at promoting the binding interaction as normal serum.

D. Anti-LBP Immunoreactivity with Distinct Forms of LBP

To assess the antibody binding characteristics and to map the epitopic specificity of the anti-LBP monoclonal antibodies of this invention prepared in Example 1, indirect enzyme linked immunosorbent assays (ELISA) were performed. For the assays, separate wells of a microtiter plate were coated with 0.1 ug/well of LBP purified from normal human serum as described in Example 1, denatured LBP, or with a complex of LBP:LPS. The latter complex was formed by first coating microtiter wells with LPS prepared as described in Example 2A followed by washing and the addition of purified LBP. The wells were maintained for one hour at 37C. The wells were then washed and the plate was blocked with non-fat dry milk dissolved in PBS. Anti-LBP monoclonal antibodies, purified from the hybridoma tissue culture supernatants with Protein A according to manufacturer's instructions (Pharmacia, Piscataway, N.J.) were then added at a concentration of 1 ug/ml. The plates were maintained for 1 hour at 37C to allow the antibodies to immunoreact with the antigens retained on the solid phase. The plates were then wash and reacted for an additional hour with horseradish peroxidase labeled goat anti-mouse IgG. Following washing, the plates were developed with the addition of ortho-phenylenediamine (OPD). The plates were then read in an ELISA machine at 490 nm wavelength.

Figure 4:
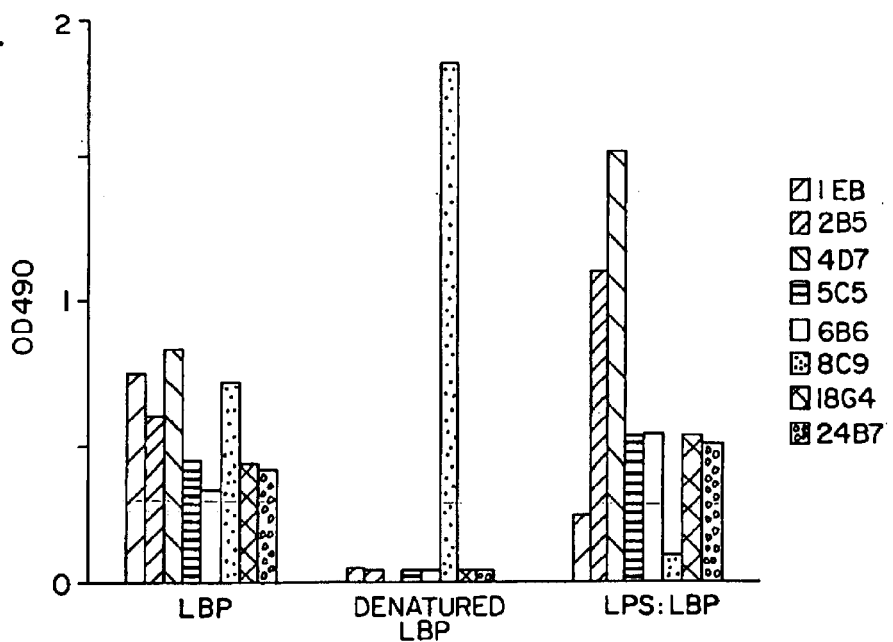
FIG. 4 illustrates various LBP-specific monoclonal antibody immunoreactivities with three distinct forms of LBP, purified LBP, denatured LBP, and a complex of LPS:LBP. The designations of the antibodies are shown at the right of the figure and these correspond to the data shown in the three sets of bar graphs from left to right with the monoclonal antibodies, 1E8, 2B5, 4D7, 5C5, 6B6, 8C9, 18G4 and 24B7. The immunoassays were performed as described in Example 2D. Immunoreactivity is expressed as the optical density of the reactive wells at 490 nm (OD490).

The results of the immunoassays on purified LBP, denatured LBP and a complex of LPS:LBP are shown in FIG. 4. The designations of the antibodies are shown at the right of the figure and these correspond to the data shown in the three sets of bar graphs from left to right with the monoclonal antibodies, 1E8, 2B5, 4D7, 5C5, 6B6, 8C9, 18G4 and 24B7. All of the anti-LBP antibodies generated from immunizing mice with purified human non-denatured LBP exhibited immunoreactivity to purified LBP as expected. Only one antibody, 8C9, however, additionally immunoreacted with denatured LBP. When LBP was complexed with LPS, 8C9 was not-as effective in binding to LBP in comparison to binding to LBP alone or in comparison to the other antibodies binding to the LPS:LBP complex. The antibodies, 2B5 and 4D7, exhibited the greatest amount of immunoreactivity with the complex while the antibody 1E8 had reduced activity. The affinity of 1E8 for LBP in the context of a complex with LPS is diminished in comparison with the immunoreactivity seen to LBP alone.

In similar assays performed using rabbit-derived LBP instead of human-derived LBP, only 1E8, 2B5 and 4D7 exhibited immunoreactivity above control background. Thus, only three of the eight anti-LBP antibodies generated from human LBP immunogen cross-reacted with rabbit LBP. Moreover, only 8C9 was reactive with denatured LBP.

E. Determination of LPS and Anti-LBP Monoclonal Antibody Distinct Binding Sites on LBP To assess the ability of anti-LBP antibodies to bind to sites on LBP distinct from the LPS binding site, an immunoassay where the antibodies were first coated on the plate was performed. The assay was essentially as described above in Example 2D with the exception that the antibodies were first coated on the microtiter wells followed by washes and the addition of LBP in the form of either normal human serum (NHS) or acute phase human serum (APHS), the latter of which contains higher amounts of LBP. Following the incubation of the serum, the concentration of which at 10% resulted in maximum LPS binding as shown in FIG. 2, LPS conjugated to biotin was added. The bound LPS was detected by the addition of streptavidin-peroxidase as described in Example 2B.

Figure 5:
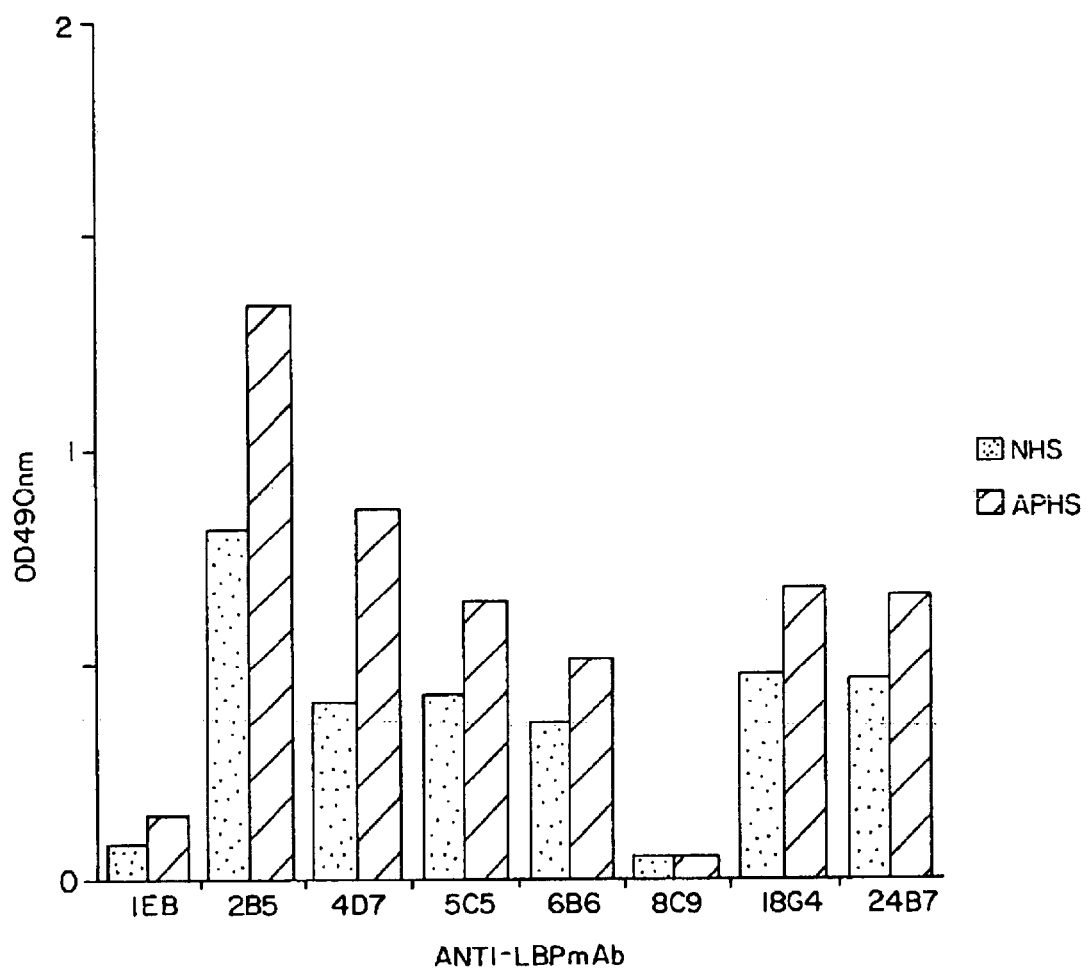
FIG. 5 illustrates the ability of anti-LBP monoclonal antibodies to capture LBP without affecting the subsequent binding of LPS to the captured LBP. The results are expressed as OD490 for each of the anti-LBP antibodies shown on the X-axis. The LPS was provided in the assays by the addition of either normal human serum (NHS) shown by the closed bars or by acute phase human serum (APHS) shown by the cross-hatched bars. The capture assays were performed as described in Example 2D.

The results, shown in FIG. 5, illustrate the ability of anti-LBP monoclonal antibodies to capture LBP without affecting the subsequent binding of LPS to the captured LBP. The results are expressed as OD490 for each of the anti-LBP antibodies shown on the X-axis. Only antibody 8 did not have heightened immunoreactivity with APHS. All the other antibodies immunoreacted with the LBP provided by either the NHS or APHS sera. All the antibodies immunoreacted with their respective LBP epitopes without affecting the binding of LPS to form a complex with LBP. Thus, complex formation was not inhibited by the immunoreaction with anti-LBP antibodies confirming the initial results described in Example 2C that the antibodies of this invention do not block the binding of LPS to LBP but do block the transfer of LPS from LBP to CD14.

E. Antibody Capture Assays to Determine the Anti-LBP Binding Sites on LBP

Antibody capture assays were performed to determine the epitopic specificity of the anti-LBP monoclonal antibodies produced in Example 1. Immunoassays including antibody capture assays are well known to one having ordinary skill in the art and are described by Harlow et al., In Antibodies: A Laboratory Manual, Cold Spring Harbor Laboratory, 1988. The assays were performed essentially as described in Example 2D above with the changes noted below. For the assay, the eight separate antibodies were coated onto microtiter wells to allow for the formation of a solid antibody-coated phase. The non-adhered excess antibodies were washed from the plate followed by addition of LBP in the form of normal human serum to each of the wells to allow the LBP in the serum to bind to the anti-LBP antibodies. Following a washing step, a parallel set of antibodies that were labeled with biotin were then admixed to each well so that every possible combination of two antibodies, 64 in all, were obtained. The second admixture of antibodies was maintained to allow the antibody to bind to an unoccupied site on the antibody-immobilized LBP in the well. The captured antibodies were detected with streptavidin peroxidase as described above.

Based on these multiple antibody capture assays performed with human LBP from serum, the 1E8 anti-LBP monoclonal antibody was determined to recognize a distinct non-overlapping immunoreactive site on LBP that the sites recognized by the anti-LBP monoclonal antibodies, 2B5, 4D7, 5C5, 6B6, 8C9, 18G4 and 24B7. No immunoreactivity was detected when the latter seven antibodies were used in capture assays with each other in 49 possible combinations. Thus, two distinct groups of antibodies having unique LBP epitopes resulted from immunizing mice with non-denatured human-LBP. The 1E8 antibody comprises its own group and the remaining antibodies, based on the fact that they compete for the same LBP binding site, comprise the other group. Of these groups, the 1E8 and 2B5 antibodies have been deposited with ATCC as described in Example 4.

Further antibody capture assays were performed to assess the ability of the anti-LBP monoclonal antibodies having different LBP binding epitopes to allow for the detection of LBP in with other sera containing LBP. The assays were performed as described above with 1E8 coated on the well as the capture antibody and 2B5 as the probe antibody, both of which were shown to bind to separate LBP epitopes. The serum samples used in the assay and shown on the X-axis included acute phase human serum (APHS), normal rabbit serum (NRS), acute phase rabbit serum (APRS), normal chimp serum (Chimp), and baboon serum before challenge with LPS (T=0) and after a 28 hour challenge with a sub-lethal dose of LPS.

Figure 6:
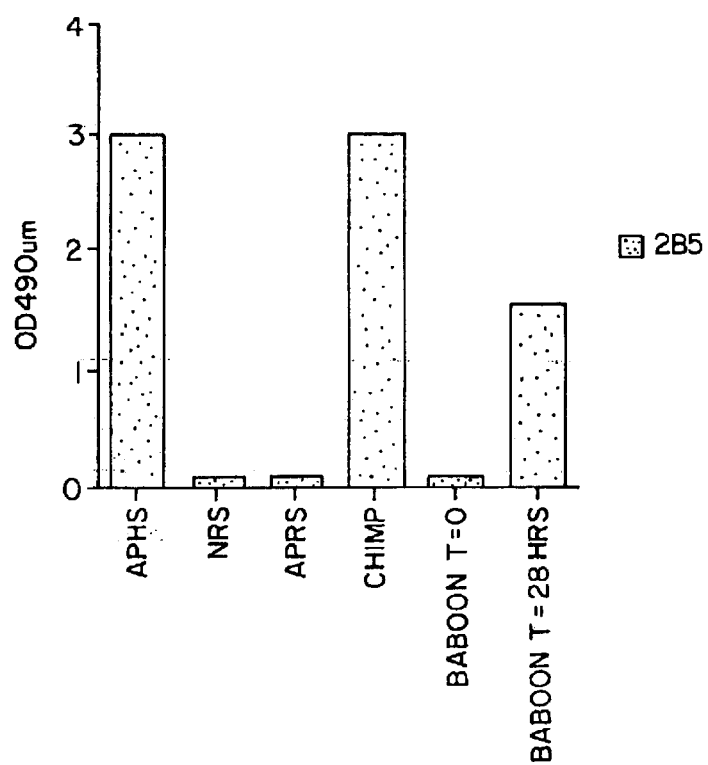
FIG. 6 illustrates the results of a 2-site sandwich assay (antibody capture assay) showing the ability to detect LBP in various serum samples captured with the 1E8 anti-LBP monoclonal antibody and probed with the 2B5 anti-LBP monoclonal antibody. The serum samples used in the assay and shown on the X-axis included acute phase human serum (APHS), normal rabbit serum (NRS), acute phase rabbit serum (APRS), normal chimp serum (Chimp), and baboon serum before challenge with LPS (T=0) and after a 28 hour challenge with a sub-lethal dose of LPS. The experiments were performed as described in Example 2E.

The results of the assay, shown in FIG. 6, illustrate the ability to detect LBP in various serum samples captured with the 1E8 anti-LBP monoclonal antibody and probed with the 2B5 anti-LBP monoclonal antibody. The antibody capture assays using antibodies representative of the two LBP-epitopic binding specificities, 1E8 and 2B5, were effective at binding LBP in APHS, in chimp serum, and in baboon serum challenged with LPS. No significant LBP was detected by antibody capture assays where the LBP was provided from normal rabbit serum, acute phase rabbit serum or unchallenged baboons. The results indicate the immunospecificity of the two groups of antibodies to LBP from human, chimp and baboon. However, LBP in the resting state of humans (FIG. 5) and chimps (FIG. 6) was detectable while it was not detectable in the resting state of baboons. Only upon challenge with LPS in the baboon was LBP detectable with the antibody capture assay. No rabbit-derived LBP was detected (captured) in the assay further supporting the evidence that the antibodies recognize certain homologous LBPs but not other more divergent proteins. The antibody capture assay described herein can be performed with any of the other members of the group of antibodies to which 2B5 is a member, i.e., having the same or overlapping LBP epitopic specificity,-with 1E8. The antibody capture assay thus provides a useful diagnostic procedure to allow the detection of LBP in various fluid samples.

F. Effect of Anti-LBP Antibodies on LPS-Induced TNF Release from Cells

As shown in Example 2C, anti-LBP antibodies of this invention allowed the binding of LPS to LBP, i.e., the formation of LPS:LBP complex, but prevented the transfer of LPS from the complex to CD14 (Table 1). Assays were then performed to determine if the anti-LBP antibodies that inhibited the binding of LPS to CD14 would effect the LPS-induced tumor necrosis factor (TNF) production by cells.

Figure 7:
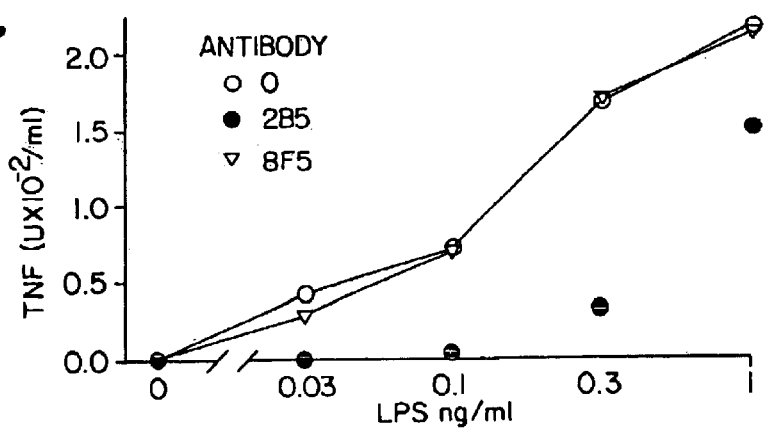
FIG. 7 illustrates the effects of anti-LBP monoclonal antibodies on LPS-induced cellular activation as measured by cellular release of tumor necrosis factor (TNF). The amount of TNF released is plotted on the Y-axis (U×10$^{-2}$/ml) against increasing concentrations of LPS from 0 to 1 ng/ml on the X-axis. The assays were performed in the presence of either the 2B5 or 8F5 anti-LBP monoclonal antibodies that are respectively represented by the lines marked with closed circles and open triangles. For a control, the assays were performed in the absence of any antibody, the results of which are shown by the line with open circles. The assays were performed as described in Example 2F.

For the assay, whole human blood was aliquoted in 0.5 ml Sarstedt polypropylene tubes (100 ul of blood/tube) followed by the addition of 3.2 ul of 2B5 anti-LBP monoclonal antibody for 10 minutes at room temperature. The anti-LBP antibody, 8F5, shown in Example 2C not to inhibit the binding of LPS to CD14 was also used in the assay along with parallel assays in which no antibody was added. LPS derived from *Salmonella minnesota* Re595 was then added to the tubes for a final concentration ranging from 30 picograms/ml (pg/ml) to 1 nanogram/ml (ng/ml). The tubes were then incubated at 37C for 4 hours. To measure TNF activity, 300 ul of RPMI 1640 medium was added to each tube followed by mixing, centrifugation and transfer of 50 ul of the diluted plasma supernatant to the WEHI clone 13 cytolytic cell assay, the latter of which is well known to one of ordinary skill in the art. The results of these cellular activation assays are shown in FIG. 7. The amount of TNF released is plotted on the Y-axis ($U \times 10^{-2}$/ml) against increasing concentrations of LPS from 0 to 1 ng/ml on the X-axis. The assays were performed in the presence of either the 2B5 or 8F5 anti-LBP monoclonal antibodies that are respectively represented by the lines marked with closed circles and open triangles. For a control, the assays were performed in the absence of any antibody, the results of which are shown by the line with open circles. The anti-LBP monoclonal antibody 2B5 was blocked the release of TNF as compared to assays performed without any antibody or with the 8F5 antibody that did not block LPS transfer to CD14. Blood provided from several donors have resulted in the same activity.

Thus, the 2B5 antibody, a representative of the group of antibodies that recognize LBP by the same or substantially overlapping epitopes, did not prevent the binding of LBP to CD14, allowed LPS to bind to LBP to form an LPS:LBP complex, inhibited the subsequent transfer of complex bound LPS to CD14, and further inhibited the LPS-induced release of TNF. This last functional aspect of the 2B5 antibody has beneficial therapeutic value in that the release of TNF that potentiates inflammatory reactions as a result of sepsis can be ameliorated. The anti-LBP monoclonal antibodies that have been characterized herein to comprise two distinct LBP epitope binding specificities, the 1E8 group and the 2B5, 4D7, 5C5, 6B6, 18G4 and 24B7 group, can be used diagnostically and therapeutically with the methods of this invention.

3. Characterization of LPS Binding by CD14

A. Kinetics of LPS Binding by CD14-Expressing CHO Cells

The period of time that was required for the binding of LPS by CD14-expressing CHO cells was measured in the LPS binding assay as described in Example 2A over a time course from 0 to 30 minutes. The binding of LPS by CD14 was extremely rapid; approximately 80% of the binding occurred within 5 minutes with maximal binding being obtained within ten minutes. The effect of temperature was also assessed. The ability of CD14 to bind LPS was relatively independent of temperature. CD14-expressing CHO cells bound LPS in the presence of LBP or serum at temperatures as low as 4C, if the LPS and serum were preincubated at a temperature $\geq$10C. Over this range, the amount of LPS bound did not increase with temperature. A small but reproducible decrease in the amount of LPS bound at 37C compared to lower temperatures was observed.

Because of the possibility that the low temperature used in the assays describe herein might result in aggregation of $^3$H-LPS, additional metabolic inhibitors were used in the assays to permit assessment of LPS binding at 37C. CD14-expressing CHO cells were prepared as described in Example 2A in 0.15 M NaCl, 20 mM HEPES, 1 mM EDTA, 0.3 mg/ml BSA, 5 mM deoxyglucose, 10 mM sodium azide, 2 mM NaF, pH 7.4 (SEBDAF buffer) for 30 minutes, and found that CD14-expressing CHO cells expressed as much CD14 (by flow microfluorometry analysis with FITC-MY4) as control CD14-CHO cells. CD14-expressing CHO cells depleted of ATP by preincubation at 37C in SEBDAF buffer were then tested in a LPS binding assay performed as described in Example 2A at 37C in SEBDAF buffer.

In addition, to determine the effects of the above metabolic treatments on the binding of LPS by CD14, phosphatidylinositol-specific phospholipase C treatment that promotes release of LPS from CD14 was performed. For this assay, $2 \times 10^5$ cells in 50 ul binding buffer were incubated with 0.5 units of PI-PLC derived from *B. cereus* (EC 3.1.4.10, Sigma) for 30 minutes at 10C and then washed in 500 ul binding buffer. Flow microfluorometry analysis with FITC-MY4 confirmed that this treatment completely removed CD14 from CD14-expressing CHO cells.

In the presence of sodium azide/EDTA at 10C or at 37C in SEBDAF buffer, 90% or 75%, respectively, of the LPS was released by phosphatidylinositol-specific phospholipase C, indicating that the LPS remained bound to CD14 on the surface of the cell. If the binding assay is performed under more physiologic conditions, i.e. at 37° in tissue culture media, only half of the LPS can be released by PI-PLC, indicating that much of the LPS is no longer on CD14 exposed to the cell surface and that the transfer of LPS is energy dependent.

Thus, LPS binding to LBP and CD14 was relatively rapid. The interaction was almost complete by 5 minutes and was maximal by 10 minutes. If the LPS was pre-incubated with serum at 10C, CD14-expressing CHO cells bound as much LPS at 4C as they did at 22C. This indicates that binding does not require extensive mobility of CD14 within the cell membrane. The temperature dependence of LPS-protein interactions may reflect the temperature-dependent phase changes which LPS is known to undergo. However, CD14 binding to LPS was relatively insensitive to temperature as the LPS has already bound to LBP.

B. Affinity of LPS-CD14 Interaction

Affinity assays were performed to determine the nature of the binding interaction between LPS and CD14. The affinity assays were done using 7–8 different concentrations of LPS over the range 50–500 ng/ml LPS. For determination of affinity, the supernates from the first and second incubation were pooled and counted to determine the amount of free LPS. The amount of LPS bound in the absence of serum at each concentration of LPS was considered to be nonspecific binding, and was subtracted from the amount of LPS bound in the presence of serum.

Two methods were used to calculate affinity constants. One method consisted of plotting bound LPS as a function of the concentration of free LPS and fitting the curve to the hyperbolic function $F(Bmax [\text{Free LPS}], K_D+[\text{Free LPS}])$ using SigmaPlot software (Jandel Scientific, Corte Madera, Calif.). The second method was Scatchard analysis. The two methods gave very similar results.

The affinity of the interaction between CD14-expressing CHO cells and LPS in the presence of 10% human serum at 10C was measured. The Y was estimated by curve fitting to be $2.7 \times 10^{-8}$ M; the estimate by Scatchard analysis was $3.2 \times 10^{-8}$ M. Both methods also gave similar estimates of Bmax; $7.3 \times 10^6$ and $8.4 \times 10^6$ molecules/cell. In three separate experiments, the mean apparent $K_D$ was 2.74 (m 0.99)× $10^{-8}$ M; the mean Bmax was 8 (m 0.47)×$10^6$ molecules of LPS bound per cell. Based on the binding experiments done with $^{125}$I-labeled Fab fragments of anti-CD14 mAb described in Example 2A that the CD14-expressing CHO cells expressed $4.4 \times 10^5$ CD14 molecules. Therefore, the molar ratio of LPS bound to CD14 at 10C was approximately 18:1. The $K_D$ at 37C was estimated to be 2.7 (m 1.2)×$10^{-8}$ M and the Bmax to be 3.5 (m 0.95)×106 molecules of LPS/CD14-expressing CHO cell. At 37C, the molar ratio of LPS bound to surface CD14 was approximately 8:1.

Studies with THP-1 cells induced to express CD14 yielded almost identical estimates in comparison to the binding of LPS by CD14 on CHO cells as described above in Example 3B. The relatively high molar ratio of LPS to CD14 is somewhat unexpected. One possible explanation is that the LPS is present as an aggregate of 8–20 monomers, depending on the temperature and the CD14 is binding the aggregate, rather than monomeric LPS. Another possible explanation is that CD14 has multiple LPS binding sites.

To address the issue of whether LPS was binding as very large aggregates, binding experiments were performed with fluorescein-labeled LPS both at 10C in azide/EDTA and at 37C in SEBDAF buffer. By fluorescence microscopy, LPS was evenly distributed around the cell surface at both temperatures, indicating that the LPS was not binding to CD14 in huge aggregates.

C. LPS Binding to CD14-Expressing THP-1 Cells

The characteristics of LPS binding in the macrophage cell line THP-1, described in Example 2A, were also determined. Induction of CD14 expression by 1,23-dihydroxy vitamin $D_3$ treatment was required for significant binding of LPS. The expression of CD14 increased over time with 1,23-dihydroxy vitamin $D_3$ treatment; the maximal LPS bound also increased over time with 1,23-dihydroxy vitamin $D_3$ treatment. The same anti-CD14 mAb inhibited binding of LPS by THP-1 cells as inhibited LPS binding by CD14-expressing CHO cells. The binding was dependent upon serum, and could be inhibited by anti-LBP mAb. The kinetics and temperature dependence of LPS binding by THP-1 were identical to that seen with CD14-expressing CHO as shown above in Example 3B. The curve fitting estimate of $K_D$ was $2.7 \times 10^{-8}$ M; the Scatchard estimate was $5.8 \times 10^{-8}$ M. The Bmax estimates were $1.67 \times 10^7$ and $1.89 \times 10^7$ molecules/THP-1 cell, respectively. In three separate experiments, the mean $K_D$ was 4.89 (m 1.42)×$10^{-8}$ M and the mean Bmax was 1.5 (m 0.26)×$10^7$ molecules/cell. THP-1 cells treated with 1, 25-dihydroxy vitamin $D_3$ for 48 hours expressed approximately $6.8 \times 10^5$ CD14 molecules per cell, so the molar ratio of LPS bound to CD14 was approximately 22:1.

4. Deposit of Materials

The murine hybridomas, designated Mab 1E8 and 2B5, were deposited on or before Nov. 16, 1993, with the American Type Culture Collection, 10801 University Blvd., Manassas, Va. 20110-2209 (ATCC). The 1E8 and 2B5 hybridomas have the respective ATCC Accession Numbers 11490 and 11491. The deposit provides murine hybridomas that secrete monoclonal antibodies of this invention. This deposit was made under the provisions of the Budapest Treaty on the International Recognition of the Deposit of Microorganisms for the Purpose of Patent Procedure and the Regulations thereunder (Budapest Treaty). This assures maintenance of viable hybridomas for 30 years from the date of deposit. The hybridomas will be made available by ATCC under the terms of the Budapest Treaty which assures permanent and unrestricted availability of the progeny of the culture to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 U.S.C. §122 and the Commissioner's rules pursuant thereto (including 37 CFR S1.14 with particular reference to 886 OG 638). The assignee of the present application has agreed that if the hybridoma deposits should die or be lost or destroyed when cultivated under suitable conditions, they will be promptly replaced on notification with a viable specimen of the same culture. Availability of the deposited hybridomas are not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by the hybridomas deposited, since the deposited embodiment is intended as a single illustration of one aspect of the invention and any hybridomas that are functionally equivalent are within the scope of this invention. The deposit of material does not constitute an admission that the written description herein contained is inadequate to enable the practice of any aspect of the invention, including the best mode thereof, nor is it to be construed as limiting the scope of the claims to the specific illustration that it represents. Indeed, various modifications of the invention in addition to those shown and described herein will become apparent to those skilled in the art from the foregoing description and fall within the scope of the appended claims.

The foregoing specification, including the specific embodiments and examples, is intended to be illustrative of the present invention and is not to be taken as limiting. Numerous other variations and modifications can be effected without departing from the true spirit and scope of the invention.

What is claimed is:

1. A monoclonal antibody that immunoreacts with lipopolysaccharide (LPS) binding protein (LBP), but does not substantially inhibit LBP binding to LPS, wherein said monoclonal antibody has a binding specificity to LBP, to denatured LBP, and to a complex of LBP and LPS, and wherein said binding specificity is that of Mab 4D7, Mab 5C5, Mab 6B6, Mab 8C9, Mab 18G4, or Mab 24B7.

2. A monoclonal antibody that immunoreacts with lipopolysaccharide (LPS) binding protein (LBP), inhibits LBP-mediated binding of LPS to CD14, but does not substantially inhibit LBP binding to LPS, wherein said monoclonal antibody has a binding specificity to LBP, to denatured LBP, and to a complex containing LBP and LPS, and wherein said binding specificity is that of Mab 4D7, Mab 5C5, Mab 6B6, Mab 18G4, or Mab 24B7.

3. The monoclonal antibody of claim 2, wherein the monoclonal antibody inhibits LBP-mediated LPS-dependent activation of myeloid cells.

4. The monoclonal antibody of claim 2, wherein the monoclonal antibody inhibits LBP-mediated LPS-dependent secretion of tumor necrosis factor from myeloid cells.

5. A hybridoma cell line that produces a monoclonal antibody that immunoreacts with lipopolysaccharide (LPS) binding protein (LBP), inhibits LBP-mediated binding of LPS to CD14, but does not substantially inhibit LBP binding to LPS, wherein said monoclonal antibody has a binding specificity to LBP, to denatured LBP, and to a complex containing LBP and LPS, and wherein said binding specificity is that of Mab 4D7, Mab 5C5, Mab 6B6, Mab 18G4, or Mab 24B7.

6. A pharmaceutical composition comprising at least one dose of an immunotherapeutically effective amount of the monoclonal antibody of claim 3, in a pharmacological carrier.

7. The pharmaceutical composition of claim 6 wherein said composition contains two or more different monoclonal antibodies.

* * * * *